United States Patent
Zaworotko et al.

(10) Patent No.: US 10,130,708 B2
(45) Date of Patent: *Nov. 20, 2018

(54) LITHIUM COCRYSTAL COMPOSITIONS

(75) Inventors: Michael John Zaworotko, Tampa, FL (US); Roland D. Shytle, Largo, FL (US); Tien Teng Ong, Singapore (SG); Ryan N. Cantwell, Melbourne, FL (US); Tranhha Nguyen, Tampa, FL (US); Adam John Smith, Tampa, FL (US); Padmini Kavuru, West Lafayette, IN (US)

(73) Assignee: University of South Florida, Tampa, FL (US)

( * ) Notice: Subject to any disclaimer, the term of this patent is extended or adjusted under 35 U.S.C. 154(b) by 516 days.

This patent is subject to a terminal disclaimer.

(21) Appl. No.: 14/007,023

(22) PCT Filed: Mar. 26, 2012

(86) PCT No.: PCT/US2012/030586
§ 371 (c)(1),
(2), (4) Date: May 5, 2014

(87) PCT Pub. No.: WO2012/129568
PCT Pub. Date: Sep. 27, 2012

(65) Prior Publication Data
US 2014/0242193 A1    Aug. 28, 2014

Related U.S. Application Data

(60) Provisional application No. 61/467,272, filed on Mar. 24, 2011.

(51) Int. Cl.
*A61K 9/14* (2006.01)
*A61K 33/00* (2006.01)
(Continued)

(52) U.S. Cl.
CPC .......... *A61K 47/183* (2013.01); *A61K 33/00* (2013.01); *A61K 33/14* (2013.01); *A61K 45/06* (2013.01);
(Continued)

(58) Field of Classification Search
CPC ........ A61K 33/14; A61K 33/00; A61K 45/06; A61K 47/186; A61K 47/22; A61K 47/183; A61K 9/145; A61K 2300/00
(Continued)

(56) References Cited

U.S. PATENT DOCUMENTS

2003/0224006 A1    12/2003 Zaworotko
2004/0176335 A1    9/2004 Childs
(Continued)

FOREIGN PATENT DOCUMENTS

WO    2004078163    9/2004

OTHER PUBLICATIONS

Pearson Prentice Hall, Inc., Amino Acids (2005), [Retrieved from internet <URL: https://bio16mit.files.wordpress.com/2013/07/aminoacids01.jpg >], 1 page.*
(Continued)

*Primary Examiner* — Ernst V Arnold
*Assistant Examiner* — Miriam A Levin
(74) *Attorney, Agent, or Firm* — Thomas | Horstemeyer, LLP

(57) ABSTRACT

2:1 cocrystals of amino acids and Li+ salts crystallize from hot water to afford water stable cationic networks based upon tetrahedral lithium cations: bilayered square grids, a lithium zeolitic metal-organic material (LiZMOM) and several lithium diamondoid metal-organic materials (LiDMOMs). The compositions may be used as a pharmaceutical for the treatment of suicidality and other disorders that require lithium to penetrate the blood brain barrier and exert
(Continued)

therapeutic effects in the CNS. Advantageously, the novel cocrystal forms described herein may be used to lower the oral dose required to achieve therapeutic concentrations of lithium in the brain, thus reducing the peripheral toxicity and potentially broadening the therapeutic index in comparison to conventional lithium forms.

4 Claims, 5 Drawing Sheets

(51) Int. Cl.
  A61K 33/14    (2006.01)
  A61K 45/06    (2006.01)
  A61K 47/18    (2017.01)
  A61K 47/22    (2006.01)
(52) U.S. Cl.
  CPC ............ *A61K 47/186* (2013.01); *A61K 47/22* (2013.01); *A61K 9/145* (2013.01); *A61K 2300/00* (2013.01)
(58) Field of Classification Search
  USPC ........................................ 424/677, 718, 722
  See application file for complete search history.

(56) References Cited

U.S. PATENT DOCUMENTS

| | | | |
|---|---|---|---|
| 2007/0026078 A1 | 2/2007 | Almarsson | |
| 2007/0059356 A1 | 3/2007 | Almarsson | |
| 2007/0299033 A1* | 12/2007 | McMahon | A61K 9/145 |
| | | | 514/50 |
| 2008/0146772 A1 | 6/2008 | Zaworotko | |
| 2010/0204204 A1 | 8/2010 | Zaworotko et al. | |
| 2010/0311701 A1 | 12/2010 | Almarsson | |

OTHER PUBLICATIONS

Babu et al., Growth and characterization of L-lysine monohydrochloride dihydrate (L-LMHCI) single crystal, Crystal Research and Technology (Apr. 2006) 41 (4): 405-410 (Abstract only, 3 pages) (Year: 2006).*
Balakrishnan et al., Growth and characterization of glycine lithium sulphate single crystal, Crystal Research and Technology (Dec. 2006) 41 (2): 1184-1188 (Year: 2006).*
MIT Department of Chemistry X-Ray Diffraction Facility, Growing Quality Crystals, [Retrieved from internet <URL: http://web.mit.edu/x-ray/cystallize.html >], [Downloaded Jan. 20, 2018], 5 pages (Year: 2018).*
Pal et al., Single crystal growth and characterization of the nonlinear optical crystal L-arginine hydrofluoride, Journal of Crystal Growth (2002) 234: 267-271 (Year: 2002).*
Sathyalakshmi et al., Synthesis, growth and characterization of single crystals of pure thiourea doped L-glutamic acid hydrochloride, Crystal Research and Technology (Jan. 2007) 42 (1): 78-78 (Abstract only, 3 pages) (Year: 2007).*
Yadav et al., Co-crystals: A Novel Approach to Modify Physicochemical Properties of Active Pharmaceutical Ingredients, Indian J Pharm Sci (Jul.-Aug. 2009), 71(4): 359-370, html version is 16 pages (Year: 2009).*
Chekmenev et al., Ion-Binding Study by 17O Solid-State NMR Spectroscopy in the Model Peptide Gly-Gly-Gly at 19.6 T, J. Am. Chem. Soc. (2006) vol. 128, No. 30, pp. 9849-9855 (Year: 2006).*
Kubala, Purified vs Distilled vs Regular Water: What's the Difference, Healthline (Mar. 1, 2018) [Retrieved from internet <URL: https://www.healthline.com/nutrition/purified-vs-distilled-vs-regular-water >], 12 pages (Year: 2018).*
Baran et al. Bis(glycine) lithium nitrate—A new non-centrosymmetric crystal: X-ray structure, vibrational spectra and DSC investigations, Journal of Molecular Structure, 2009, 927(1), 43-53, 11 pages.

Uma Devi et al. Synthesis, Crystal Growth and Characterization of L-Proline Lithium Chloride Monohydrate: A New Semiorganic Nonlinear Optical Material, Crystal Growth & Design, 2009, 9(3), 1370-1374, 5 pages.
Patent Cooperation Treaty, International Search Report for PCT/US2012/030586, 6 pages, dated Sep. 26, 2012.
Chlupaty et al., Structure and properties of lithium n-butyl amidinates, Journal of Organometallic Chemistry, 2011: 696, 2346-2354, pp. 9.
Barrer et al., The hydrothermal chemistry of silicates. Part I. Synthetic Lithium Aluminosilicates, Journal of the Chemical Society (Resumed) 1951, 1267-1278, 16 pages.
Smith et al., Plasma and brain pharmacokinetics of previously unexplored lithium salts. RSC Advances, 2014, 4) 24):12632-12365, 4 pages.
Sreenivasulu et al., A Metal Coordination Polymer with Hexagonal Diamondoid (or Lonsdaleite) Network Topology Crystal Growth & Design 2003, vol. 3, No. 5 635-637, 3 pages.
Wang et al., Mn3(HC00)6: a 3D porous magnet of diamond framework with nodes of Mn-centered MnMn4 tetrahedron and guest-modulated ordering temperature, Chemical Communications 2004, 416-417, 2 pages.
Saravanan et al., Lithium storage in a metal organic framework with diamondoid topology-a case study on metal formats, Journal of Materials Chemistry 2010, 20, 8329-8335, 7 pages.
Morris et al., Assembly of 63,66-Pillared Metal-Organic Bilayers and Diamondoid Lattices Using Molecular Li2O2 Ring Dimers as Secondary Building Units, Crystal Growth & Design 2006, 6, 1071-1073, 3 pages.
Wu et al., Zeolite RHO-Type Net with the Lightest Elements, Journal of the American Chemical Society 2009, 131, 6111-6113, 3 pages.
Sava et al., Quest for Zeolite-like Metal-Organic Frameworks: On Pyrimidinecarboxylate Bis-Chelating Bridging Ligands, Journal of the American Chemical Society 2008, 130, 3768-3770, 3 pages.
Navarro et al., H2, N2, CO, and CO2 Sorption Properties of a Series of Robust Sodalite-Type Microporous Coordination Polymers, Inorganic Chemistry 2006, vol. 45, No. 6 2397-2399, 3 pages.
Liu et al., Molecular building blocks approach to the assembly of zeolite-like metal-organic frameworks (ZMOFs) with extra-large cavities, Chemical Communications 2006, 1488-1490, 3 pages.
Zhang et al., Zeolitic Boron Imidazolate Frameworks, Angewandte Chemie 2009, 121, 2580-2583, 4 pages.
Park et al., Exceptional chemical and thermal stability of zeolitic imidazolate frameworks, Proceedings of the National Academy of Sciences 2006, 103, 10186-10191, 6 pages.
Copp et al., Supramolecular chemistry of manganese complex [Mn(C0)3(.mu.3-OH)]4: assembly of a cubic hydrogen-bonded diamondoid network with 1,2-diaminoethane, . Journal of the American Chemical Society 1992, 114, 8719-8720, 2 pages.
Copp et al., Supramolecular chemistry of [{M(C0)3( 3-0H)}4](M = Mn or Re): a modular approach to crystal engineering of superdiamondoid networks, Journal of the Chemical Society, Dalton Transactions 1995, 2233-2243, 11 pages.
Fang et al., A Metal-Organic Framework with the Zeolite MTN Topology Containing Large Cages of vol. 2.5 nm3 Angewandte Chemie International Edition 2005, 44, 3845-3848, 4 pages.
Liang et al., Self-Assembly of Interpenetrating Coordination Nets Formed from Interpenetrating Cationic and Anionic Three-Dimensional Diamondoid Cluster Coordination Polymers, Angewandte Chemie-International Edition 2004, 116, 4 pages, 5900-5903.
Keller, An Acentric, Three-Dimensional Coordination Polymer: Synthesis and Structure of [Cu(pyrimidine)2]BF4 Angewandte Chemie International Edition in English 1997, vol. 36, No. 3, 247-248, 2 pages.
Evans et al., Crystal engineering of NLO materials based on metal-organic coordination networks. Accounts of Chemical Research, 35, 511-522, 12 pages.
Lopez et al., Novel 2-fold Interpenetrating Diamondoid Coordination Polymers: [Cu (3,3'-bipyridine)2]X (X= BF4-, PF6-) Inorganic Chemistry 1997, vol. 36, 3 pages 6138-6140.
Davis, Ordered porous materials for emerging applications, Nature 2002, 417-424, 8 pages.

(56) References Cited

OTHER PUBLICATIONS

Ockwig et al., Reticular Chemistry: Occurrence and Taxonomy of Nets and Grammar for the Design of Frameworks, Accounts of Chemical Research 2005, 38, 176-182, 7 pages.
Zaworotko, Crystal engineering of diamondoid networks, Chemical Society Reviews, 1994, 23, pp. 283-288 6 pages.
Cundy et al., The Hydrothermal Synthesis of Zeolites: History and Development from the Earliest Days to the Present Time, Chemical Reviews, 2003, 103, 663-701, 40 pages.
Baerlocher et al., Atlas of Zeolite Framework Types; Sixth Revised ed.; Elsevier Science: Amsterdam, 2007 405 pages. (All Pages Are Relevant).
Wong et al., The scientific impact of the Cambridge Structural Database: a citation-based study, Journal of Applied Crystallography, 2010, 43, 811-824, 14 pages.
Copp et al., Supramolecular chemistry of [M(C0)3( 3-0H)]4(M = Mn, Re): spontaneous strict self-assembly of distorted super-diamondoid networks that are capable of enclathrating acetonitrile, Journal of the Chemical Society, Chemical Communications 1993, 1078-1079, 2 pages.
Hayashi et al., Zeolite A imidazolate frameworks, Nat Mater 2007, 6, 501-506, 6 pages.
Huang et al., Ligand-Directed Strategy for Zeolite-Type Metal-Organic Frameworks: Zinc(ii) Imidazolates with Unusual Zeolitic Topologies, Angewandte Chemie International Edition 2006, 45, 1557-1559, 3 pages.
Alkordi et al., Zeolite-like Metal-Organic Frameworks (ZMOFs) Based on the Directed Assembly of Finite Metal-Organic Cubes (MOCs), Journal of the American Chemical Society 2009, 131, 17753-17755, 3 pages.
Hasche et al. Polymeric structures containing self-assembled Li-dioxane networks; syntheses and crystal structures of [{Li(dioxane)2.5TaCl4S}n] • n/2 dioxane and [{Li2(dioxane)3C1}n][TaC16]n, Inorganica Chimica Acta 2000, 298, 9-15, 7 pages.
Abrahams et al., A Simple Lithium(I) Salt with a Microporous Structure and Its Gas Sorption Properties, Angewandte Chemie International Edition 2010, 49, 1087-1089, 3 pages.
Banerjee et al., Synthesis and Structural Characterization of a 3-D Lithium Based Metal-Organic Framework Showing Dynamic Structural Behavior, Crystal Growth & Design 2010, vol. 10, No. 6, 2801-2805, 5 pages.
Chen et al., Three-Dimensional Metal Azide Coordination Polymers with Amino Carboxylate Coligands: Synthesis, Structure, and Magnetic Properties, Inorganic Chemistry 2009, 48, 4674-4684, 11 pages.
European Patent Office, Supplemental Search Report issued for EP12760816.4, search completed Jul. 24, 2014, 3 pages.
Clarke et al., Structure-Stability Relationships in cocrystal hydrates: does the promiscuity of water make crystaline hydrates the nemesis of crystal engineering?, Crystal Growth & Design, 2010: vol. 10, No. 5, 2052-2167, 16 pages.
Ong et al., 2:1 Cocrystals of homochiral and achiral amino acid zwitterions with Li+ salts: Water-stable zoplitic and diamondoid metal-organic metals, Journal of the American Chemical Society, 2011:133, 9224-9227, 4 pages.
Shytle et al., A Novel Lithium Cocrystal With Improved Oral Bioavailability and Targeted Brain Delivery, Database accession No. PREV201200490850; & Cell Transplantation, vol. 21, No. 4, 2012, p. 792, 19th Annual Meeting of the American-Society-For-Neural-Therapy-And-Repair; Clearwater Beach, FL, USA Apr. 26-28, 2012, 1 page.
Kavuru et al., Hierarchy of supramolecular synthons: Persistent hydrogen bonds between carboxylates and weakly acidic hydroxyl moieties in cocrystals of zwitterions, Crystal Growth & Design, 2010:10, 3568-3584, 17 pages.
Smith et al., Improving lithium therapeutics by crystal engineering of novel ionic cocrystals, Molecular Pharmaceutics, American Cancer Society. 2013:10, 4728-4738, 11 pages.
Davies, et. al. "Catalytic C-H functionalization by metal carbenoid and nitrenoid insertion", Department of Chemistry, University of Buffalo, New York, USA, Jan. 24, 2008, vol. 451, pp. 417-424, 8 pages.
Liang, et al. Self-Assembly of Interpenetrating Coordination Nets Formed from Interpenetrating Cationic and Anionic Three-Dimensional Diamondoid Cluster Coordination Polymers:, www.angewandte.de; Angew. Chem. 2004, 116, pp. 5900-5903.

* cited by examiner

LITHIUM COCRYSTAL COMPOSITIONS

CROSS-REFERENCE TO RELATED APPLICATIONS

This applications is the 35 U.S.C. § 371 national stage application of PCT Patent Application entitled "Lithium Compositions", having serial number PCT/US12/30586, filed Mar. 26, 2012, which claims priority to and the benefit of, U.S. Provisional Patent Application entitled "Lithium Compositions", having serial number 61/467,272, filed Mar. 24, 2011, both of which are herein incorporated by referene in their entireties.

FIELD OF THE INVENTION

The present invention is generally related to pharmaceutical compositions containing lithium salts and neutral organic molecules in a stoichiometric ratio. Such compositions may be used in the preparation of (or even as) pharmaceuticals.

BACKGROUND OF THE INVENTION

The global economy utilizes millions of tons per year of synthetic crystalline microporous inorganic zeolites for applications such as petrochemical cracking, ion-exchange for water softening and purification and in gas separations. Synthetic inorganic zeolites typically consist of oxide anions that link tetrahedral aluminum or silicon cations (nodes) in a 2:1 ratio.[2] The key to the existence of microporosity in zeolites is that the oxide linkers are angular (M-O-M angles typically range from 140° to 165°, thereby facilitating the generation of a wide range of topologies that are based upon rings, fused rings and polyhedral cages. Which particular topology exists for a given chemical composition is typically controlled by reaction conditions, counterions and/or structure directing agents[3] (SDAs). The absence of counterions, SDAs or the use of a linear linker more typically manifests the tetrahedral node in the form of a diamondoid (dia) net[4,5] that, unlike most zeolitic topologies, can interpenetrate to mitigate the creation of free space.

The ground rules for generating zeolitic and/or diamondoid networks are therefore self-evident and they have been validated across a remarkably diverse range of tetrahedral nodes (e.g., phosphates,[6] transition metal cations,[7-9] metal clusters[10]) and linkers (including purely organic ligands that form coordination bonds[11] or hydrogen bonds[12-14]). Coordination polymers that exploit the diversity of tetrahedral moieties and angular or linear organic ligands have recently afforded new levels of scale that includes new classes of zeolitic structures with hitherto unattainable levels of porosity. Such zeolitic metal-organic materials are exemplified by zeolitic imidazolate frameworks[15-17] (ZIFs), boron imidazolate frameworks[18] (BIFs) and zeolite-like metal-organic frameworks[19] (ZMOFs). ZIFs are based upon imidazolate ligands that subtend an angle of ca. 145° whereas the prototypal ZMOFs use 4,5-imidazole-dicarboxylate[20] and pyrimidine-based ligands[21,22] in the presence of SDAs to coordinate to 8-coordinate metals such as In and Cd. BIFs are inherently of low density because they are based upon tetrahedral boron atoms. That low density is a desirable property means that lithium, the lightest metal in the periodic table, is a particularly attractive target to serve as a tetrahedral node in either zeolitic or dia networks. Furthermore, lithium forms many air and water stable coordination environments and not all existing zeolitic metal-organic materials are water-stable. In this context, a prototypal structure was reported by Pinkerton et al., who isolated a lithium-based zeolitic ABW network with hexachlorotantalum anion embedded in what was described as a three-dimensional Li—Cl-dioxane network.[23] However, this compound is extremely moisture sensitive. Bu and coworkers addressed the challenge elegantly in BIFs by employing both lithium and boron with imidazolates in BIF-9-Li, a compound with RHO topology.[24] Other approaches to low density porous materials based upon lithium include the following: Robson et al. reported a microporous lithium isonicotinate with square channels;[25] Henderson and coworkers isolated a pillared bilayer and a diamondoid net with solvated lithium aryloxides;[26] Parise et al. reported a MOF based on lithium and 2,5-pyridinedicarboxylic acid that loses porosity upon solvent removal.[27]

SUMMARY OF THE INVENTION

Among the various aspects of the present invention may be noted the provision of compositions containing lithium salts and neutral organic molecules in a stoichiometric ratio, and a method for generating lithium based zeolitic metal-organic materials (LiZMOMs) and lithium based diamondoid metal-organic materials (LiDMOMs) by exploiting, for example, the Li-carboxylate-Li linkages that can be formed when cocrystal formers such as amino acid zwitterions form cocrystals with lithium salts. The resulting compositions may be used, for example, in the preparation of (or even as) lithium-containing pharmaceuticals which are less hygroscopic than lithium chloride.

Briefly, therefore, one aspect of the present invention is a cocrystal having the formula LiX.aM, or a solvate or hydrate thereof, wherein X is a halide or an oxyanion, M is a neutral organic molecule, and a is 1 or 2, provided, (i) M is other than glycine when X is nitrate, (ii) M is other than proline when X is chloride and a is 1, and (iii) M is other than alanylglycine when X is bromide and a is 1.

The present invention is further directed to a pharmaceutical composition comprising a composition having the formula LiX.aM or a solvate or hydrate thereof, wherein X is a pharmaceutically acceptable anion, M is a neutral organic molecule, and a is 1 or 2. In one such embodiment, X is a halide or a pharmaceutically acceptable oxyanion.

The present invention is further directed to a dosage unit form, the dosage unit form comprising a composition having the formula LiX.aM or a solvate or hydrate thereof, wherein X is a pharmaceutically acceptable anion, M is a neutral organic molecule, and a is 1 or 2. In one such embodiment, X is a halide or a pharmaceutically acceptable oxyanion.

The present invention is further directed to a method for preparing cocrystals comprising a lithium salt and a complementary neutral organic compound in a stoichiometric ratio. The method comprises dissolving the lithium salt and the complementary neutral organic compound in a solvent and evaporating or cooling the solvent. In one embodiment, the stoichiometric ratio of complementary neutral organic compound to lithium salt is 2:1, respectively. In one embodiment, the stoichiometric ratio of complementary neutral organic compound to lithium salt is 1:1.

Other aspects and objects of the invention will be in part apparent and in part pointed out hereinafter.

ABBREVIATIONS AND DEFINITIONS

Figure 1:
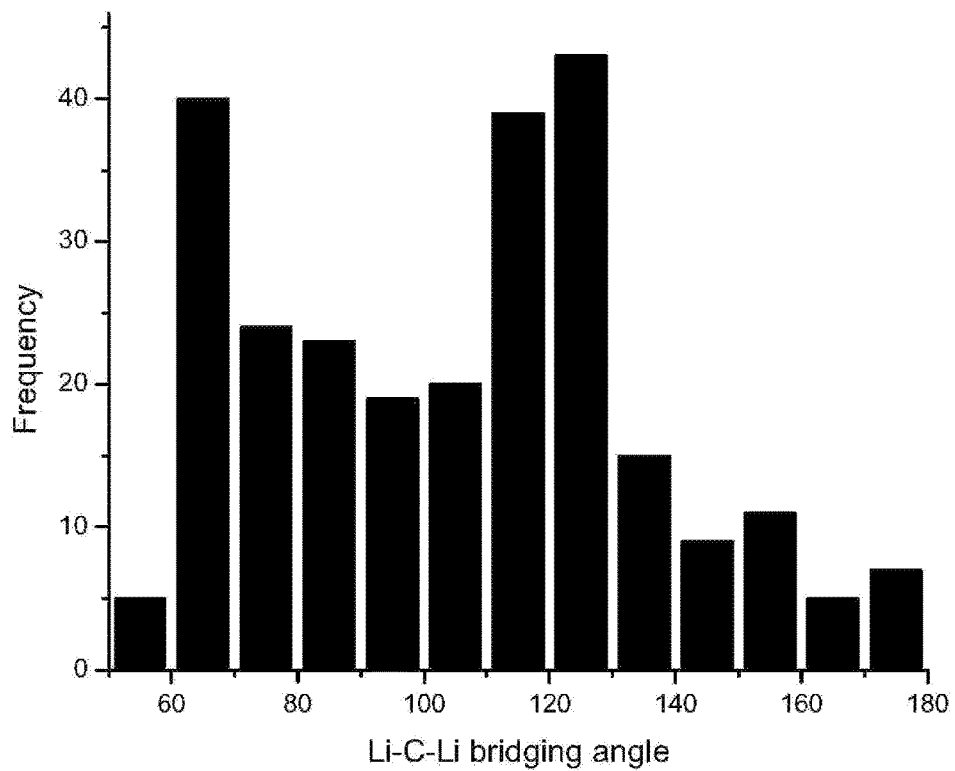
FIG. 1 is a graph depicting the Distribution of the Li—C—Li angle in crystal structures that contain lithium cations bridged by carboxylate moieties (data obtained using CSD version 5.311).

The following definitions and methods are provided to better define the present invention and to guide those of ordinary skill in the art in the practice of the present invention. Unless otherwise noted, terms are to be understood according to conventional usage by those of ordinary skill in the relevant art.

An "amino acid" as used herein refers to a molecule containing an amine group, a carboxylic acid group and a side-chain that varies between different amino acids. Amino acids include, for example, amino acids (in their non-ionized form) corresponding to the formula $H_2NCHRCOOH$ where R is an organic substituent; the key elements of an amino acid are carbon, hydrogen, oxygen, and nitrogen.

A "cocrystal" as used herein refers to a multiple component crystal containing two or more non-identical compounds in a stoichiometric ratio each of which is solid under ambient conditions (i.e., 22° C., 1 atmosphere of pressure) when in their pure form.

A "neutral" composition as used herein refers to a composition, or moiety, optionally possessing both cationic and anionic groups, having a zero net electrical charge.

An "oxyanion" as used herein refers to a chemical composition with the generic formula $A_xO_y^{z-}$ (where A represents a chemical element, O represents an oxygen atom, and x, y and z are non-zero natural numbers). Exemplary oxyanions include nitrate, sulfonate, sulfate, and carbonate.

A "zwitterion compound" or "zwitterionic composition" as used herein refers to a macromolecule, material, or moiety possessing cationic and anionic groups, or acidic and basic centers that tautomerize to the corresponding cationic and anionic groups. Typically, and preferably in the context of the present invention, these charged groups are balanced, resulting in a material with zero net electrical charge.

DETAILED DESCRIPTION OF THE PREFERRED EMBODIMENTS

The present invention is generally directed to compositions comprising at least one lithium salt and at least one complementary (i.e., capable of coordinating lithium) neutral cocrystal former in a stoichiometric ratio. Cocrystals of such compositions may used as the active pharmaceutical ingredient in pharmaceutical compositions (optionally also including other components such as pharmaceutically acceptable excipients, diluents, nutritional supplements, and other additives as described elsewhere herein), or in other compositions having utility in applications in which lithium is desired.

In general, the lithium salt cocrystals of the present invention are crystalline material comprised of two or more unique (non-identical) solids at room temperature (i.e., 22° C.) in generally a stoichiometric ratio, each co-existing in the cocrystal at the molecular level within the single crystal and each containing distinctive physical characteristics, such as structure, melting point and heats of fusion. The cocrystals may also include one or more solvate or water molecules in the crystalline lattice. That is, solvates or hydrates of cocrystals, or a cocrystal further comprising a solvent, or water or compound that is a liquid at room temperature, may be included in the compositions of the present invention, but crystalline material comprised of only one solid and one or more liquids (at room temperature) are not included in the present invention. In one embodiment, for example, a lithium salt cocrystal of the present invention, or solvate or hydrate thereof has the formula LiX.aM.bS wherein X is a halide or an oxyanion, M is a neutral organic molecule, a is 1 or 2, b is 0, 0.5, 1.0, 1.5, 2.0, 2.5 or 3.0, and S is solvent or water.

For pharmaceutical applications, it is generally preferred that the cocrystals of the present invention comprise pharmaceutically acceptable lithium salts and a stoichiometric amount of a second pharmaceutically acceptable molecule (the cocrystal former/neutral organic molecule) that is a solid under ambient conditions (i.e., 22° C., 1 atmosphere of pressure). Although a number of cocrystals are within the ambit of this invention, an example of such cocrystals are cocrystals of pharmaceutically acceptable lithium salts and neutral pharmaceutically acceptable zwitterionic compounds, flavonoids, xanthines, sugars, and/or polyphenols.

Although suicide and suicidality are major and growing public health problems and suicide is now ranked as the 11th leading cause of death in the U.S, the relationship between psychiatric medication and suicidality has not been well studied. This is at a time when there is growing evidence that vulnerability to suicidality may be inherited independently of vulnerability to mood disorders. These considerations have led to increasing calls for a separate category for "Suicide Disorders" in DSM V. However, there is growing evidence that treatments that are effective for mood disorders are not always effective for suicidality and vice versa. Paradoxically, antidepressants, although they improve depression over 4 to 8 weeks, are not believed to lower suicidality. In contrast, lithium does appear to lower suicidality in both recurrent unipolar major depressive disorder and in bipolar depression but is not a good short-term treatment of depression. To date, no medication has been specifically approved by the US Food and Drug Administration (FDA) or by any of the world's regulatory agencies. However, in the context of growing concern about suicide in the U.S., the FDA is has recently expressed interest in reviewing any medication that might demonstrate efficacy against suicidality if suicidality is the a-priori primary outcome measure. Lithium is the only medication that consistently reduces suicidality in recurrent unipolar major depressive disorder and in bipolar disorder but existing lithium drugs such as lithium chloride and lithium carbonate suffer from chronic toxicity, poor physicochemical properties and poor brain bioavailability. The cocrystals of lithium salts described herein offer improved physicochemical properties compared to existing forms of lithium and therefore have the potential to be developed as anti-suicidal drugs or for use against other mood disorders.

For non-pharmaceutical applications, the structures and properties of some cocrystals of lithium salts (in particular those with a 2:1 ratio of neutral complementary organic compounds to lithium salt, respectively, are related to diamond or zeolites and their positive charge has to be balanced by an anion. Their structure and variable composition means that they are fine-tunable in terms of their composition and molecular recognition features. They can, therefore, be used for anion exchange or sequestration (storage) of small molecules such as hydrogen, methane and carbon dioxide. Notably, lithium is the lightest metal and the cocrystals of lithium salts described herein are inherently air and water stable. They can also be prepared using homochiral organic compounds such as amino acids. They therefore offer a unique set of properties that collectively affords significant advantages over previous classes of porous material such as zeolites and metal-organic materials.

In an embodiment, non-aqueous, non-solvent impurities may be present in the cocrystal composition. In general, it is preferred that the cocrystal composition contains less than 1% by weight impurities but impurities can represent up to 25% by weight. In certain embodiments, greater degree of purity may be desired; in such instances, it may be preferred that the crystalline material contain less than 0.5% by weight impurities. In some embodiments, it may be preferred that the crystalline material contain less than 0.1% by weight impurities. In other embodiments, it may be preferred that the crystalline material contain less than 0.01% by weight impurities.

Lithium Salts

In one embodiment, the lithium salt corresponds to the formula LiX wherein X is an anion. In one embodiment, the anion is a halide or oxyanion. For pharmaceutical applications, it is generally preferred that X be halide or a pharmaceutically acceptable oxyanion. Thus, for example, X may be fluoride, chloride, bromide or iodide. Alternatively, X may be nitrate, sulfate, sulfonate, or carbonate.

Cocrystal Formers/Neutral Organic Molecules

For pharmaceutical applications, it is generally preferred that the cocrystal former is any neutral organic molecule that may be safely administered to humans. Such compositions may be identified on the GRAS list (also known as the "Generally Recognized As Safe" list) or the EAFUS list (also known as the "Everything Added to Food in the United States" list) maintained by the U.S. Food and Drug Administration or excipients approved for pharmaceutical use. More typically, however, the cocrystal former/neutral organic molecule will be a pharmaceutically acceptable zwitterionic compound, sugar, polyphenolic compound, xanthine, or flavonoid.

In one embodiment, the cocrystal former is a neutral zwitterionic compound. Exemplary zwitterionic compounds include nicotinic acids or naturally occurring or synthetic amino acids. For example, in one such embodiment, the cocrystal former comprises at least one of the 21 amino acids that are directly encoded for protein synthesis by the genetic code of eukaryotes, i.e., at least one of alanine, arginine, asparagine, aspartic acid, cysteine, isoleucine, glutamic acid, glutamine, glycine, histidine, leucine, lysine, methionine, phenylalanine, proline, selenocysteine, serine, taurine, threonine, tryptophan, tyrosine, and valine. For example, in one embodiment the cocrystal former is phenylalanine, leucine, tyrosine, or other amino acids that are preferentially transported into the brain as compared to other amino acids. By way of further example, in one embodiment the amino acid is an L-amino acid such as L-phenylalanine, L-leucine, or L-tyrosine. In an alternative embodiment, the amino acid is a D-amino acid such as as D-phenylalanine, D-leucine, or D-tyrosine. In an alternative embodiment, the cocrystal former comprises a non-proteinogenic amino acid such as betaine.

In one embodiment, the cocrystal former is xanthine or a derivative thereof. Exemplary xanthines include caffeine, paraxanthine, theophylline and threobromine.

In one embodiment, the cocrystal former is a polyphenol. Polyphenols that can be used in the compositions of the present invention can be classified into the following categories: (1) phenolic acids, (2) flavonoids, (3) stilbenoids; (4) tannins, (5) monophenol such as hydroxytyrosol or p-tyrosol, (6) capsacin and other capsaicinoids and (7) curcumin. Phenolic acids form a diverse group. Examples from the diverse group include (a) hydroxycinnamic acids: e.g., p-coumaric acid, caffeic acid, and ferulic acid; (b) hydroxybenzoid acids: e.g., p-hydroxybenzoic acid, gallic acid, ellagic acid; (c) rosmarinic acid. Tannins are large molecules, found in red wine, tea, and nuts; the term is applied to any large polyphenolic compound containing sufficient hydroxyls and other suitable groups (such as carboxyls) to form strong complexes with proteins and other macromolecules and are usually divided into hydrolyzable tannins and condensed tannins (proanthocyanidins). At the center of a hydrolyzable tannin molecule, there is a polyol carbohydrate (usually D-glucose); the hydroxyl groups of the carbohydrate are partially or totally esterified with phenolic groups such as gallic acid (in gallotannins) or ellagic acid (in ellagitannins).

Flavonoids are a long and well-known class of natural product that is attracting increasing attention as nutraceuticals and pharmaceuticals. Flavonoids are based upon a group of compounds called chalcones and typically contain a 3-ring structure called flavone. The metabolic pathway in plants affords many derivatives including flavonols, flavan-3-ols, tannins and other polyphenolics. Flavonoids are synthesized and widely distributed in plants and fulfill many functions including pigmentation in flowers, and protection from attack by microbes and insects. The widespread distribution of flavonoids means that they are ingested in significant quantities by animals. Furthermore, their variety, their relatively low toxicity compared to, for example, alkaloids, and their biological activity (they can be anti-allergic, anti-inflammatory, anti-microbial, anti-cancer and they can improve cognitive functions) means that consumers, food manufacturers and pharmaceutical companies have become interested in flavonoids for their medicinal properties. Indeed, the beneficial effects of fruit, vegetables, and tea or even red wine have been attributed to flavonoid compounds. Although many flavonoids are abundant and commercially available they can be hard to purify and crystallize and their solubility can be low.

In one embodiment, therefore, the present invention is directed to cocrystals comprising a flavonoid as the cocrystal former. In this embodiment, for example, the cocrystal may comprise a flavonoid selected from the group consisting of resveratrol, epigallocatechin-3-gallate (EGCG), quercetin, ferulic acid, ellagic acid, hespereten, and protocatechuic acid. By way of further example, the cocrystal former may be a flavonoid selected from the group consisting of EGCG, ferulic acid, ellagic acid, hespereten, and protocatechuic acid.

In one embodiment, the present invention is directed to cocrystals comprising a sugar as the cocrystal former. Exemplary sugars include monosaccharides and disaccharides. For example, in one embodiment the cocrystal former is selected from among fructose, galactose, glucose, lactitol, lactose, maltitol, maltose, mannitol, melezitose, myoinositol, palatinite, raffinose, stachyose, sucrose, trehalose, and xylitol.

In another preferred embodiment, the nutraceutical may be one of the previously mentioned flavonoid or a nutraceutical selected from a group of nutraceuticals currently believed to possess biological activity. For example, in this embodiment, the nutraceutical may be selected from the group consisting of vitamin B2 (riboflavin), glucosamine HCl, chlorogenic acid, lipoic acid, catechin hydrate, creatine, acetyl-L-carnitine HCl, vitamin B6, pyridoxine, caffeic acid, naringenin, vitamin B1 (thiamine HCl), baicalein, luteolin, hesperedin, rosmarinic acid, epicatechin gallate, epigallocatechin, vitamin B9 (folic), genistein, methylvanillin, ethylvanillin, silibinin, diadzein, melatonin, rutin hydrate, vitamin A, retinol, vitamin D2 (ergocalciferol), vitamin E (tocopherol), diosmin, menadione (K3), vitamin D3 (caholecalciferol), phloretin, indole-3-carbinol, fisetin, glycitein, chrysin, gallocatechin, vitamin B4 (adenine), vitamin B5 (pantothenic acid), vitamin B7 (biotin), theobromine, resveratrol, epigallocatechin-3-gallate (EGCG), quercetin, ferulic acid, ellagic acid, hespereten, and protocatechuic acid. By way of further example, in this embodiment, the nutraceutical may be selected from the group consisting of vitamin B2 (riboflavin), glucosamine HCl, chlorogenic acid, lipoic acid, catechin hydrate, creatine, acetyl-L-carnitine HCl, vitamin B6, pyridoxine, caffeic acid, naringenin, vitamin B1 (thiamine HCl), baicalein, luteolin, hesperedin, rosmarinic acid, epicatechin gallate, epigallocatechin, vitamin B9 (folic), genistein, methylvanillin, ethylvanillin, silibinin, diadzein, melatonin, rutin hydrate, vitamin A, retinol, vitamin D2 (ergocalciferol), vitamin E (tocopherol), diosmin, menadione (K3), vitamin D3 (caholecalciferol), phloretin, indole-3-carbinol, fisetin, glycitein, chrysin, gallocatechin, vitamin B4 (adenine), vitamin B5 (pantothenic acid), vitamin B7 (biotin), theobromine, quercetin, ferulic acid, ellagic acid, hespereten, and protocatechuic acid.

Cocrystal Formation

In general, cocrystals of the present invention may be prepared by dissolving the lithium salt and the complementary neutral organic compound (cocrystal former) in a solvent and evaporating or cooling the solvent. In one embodiment, the lithium salt and the complementary neutral organic compound are dissolved in an aqueous system. Although not necessarily preferred, the lithium salt and complementary neutral organic compound may be dissolved in polar organic solvents such as acetone, acetonitrile, DMSO and alcohols. Once formed, the solution is then preferably slowly cooled or solvent is slowly evaporated until the cocrystal is formed. The cocrystal structure of the resulting composition may be characterized by at least two techniques selected from the group consisting of powder x-ray diffraction, single crystal x-ray crystallography, differential scanning calorimetry, fourier transform infrared spectroscopy and thermogravimetric analysis.

The strategy described herein is based upon generating compounds in which there is a stoichiometric ratio of one lithium cation and two carboxylate anions. That carboxylate moieties can sustain diamondoid ("dia") nets is exemplified in a series of divalent metal formates that naturally possess the required 2:1 ratio of linker to node.[28,29] Indeed, such structures can even exhibit the rarely encountered lonsdaleite[30,31] (lon) topology. However, that lithium is monovalent means that the requisite 2:1 ratio of linker to node will be very difficult to achieve with anionic linkers. In one embodiment, this problem is addressed by using the carboxylate moieties in amino acids, i.e., neutral zwitterions, to bridge two lithium cations.

In one embodiment, the methods described herein target a new class of compound: 2:1 cocrystals of amino acids and inorganic lithium salts. The use of amino acids provides numerous advantages and opportunities: 1) many amino acids are commercially available and they are typically inexpensive; 2) FIG. 1 reveals that lithium-carboxylate-lithium angles offer the requisite diversity needed to generate a wide range of extended structures; 3) the lithium-carboxylate bond is robust even in the presence of water; 4) amino acids possess functionalized side chains that facilitates fine-tuning of the resulting structures through pre-synthetic methods; 5) the abundance of homochiral amino acids means that homochiral crystals with optical activity and bulk polarity are guaranteed; 6) most amino acids are soluble in water, therefore facilitating green synthesis; 7) the charge of the network is inverted compared to zeolites because the framework is cationic and the required counterions are anions, i.e. anion exchange becomes feasible. The remarkable range of Li-carboxylate-Li angles stems partly from the tendency of the carboxylate ligand to exhibit either endodentate or exodentate bridging modes.

In principle, 2:1 cocrystals of amino acids and lithium salts therefore fit the criteria for formation of dia and/or zeolitic frameworks. However, another structural feature of zeolites is the presence of one or more rings, typically 4-, 6- or 8-membered $M_nO_n$ rings. 4-membered $Li_4(carboxylate)_4$ rings have previously been observed in a 2:1 cocrystal of glycine and lithium nitrate demonstrating a square grid network[32] (Li—C—Li angles 115.88°, 117.83°). With the structural prerequisites for self-assembly of zeolitic and/or dia networks in mind, a series of 2:1 amino acid (sarcosine, SAR, N,N-dimethylglycine DMG, betaine, BTN and L-proline, PRO) cocrystals of lithium salts (lithium chloride, LIC, lithium bromide, LIB and lithium nitrate, LIN) have been prepared. Cocrystals of the desired stoichiometry were prepared by slow evaporation of aqueous solutions of LIC, LIB or LIN and two equivalents of the amino acid at ca. 80° C. These cocrystals are stable to at least 175° C. and are freely soluble in water. Crystallographic analysis of the products revealed that three distinct networks were observed: square grids based upon only 4-membered $Li_4(carboxylate)_4$ rings; diamondoid networks based upon only $Li_6(carboxylate)_6$ rings; a zeolitic ABW network based upon 4-membered, 6-membered and 8-membered $Li_n(carboxylate)_n$ (n=4, 6 and 8) rings.

Figure 2:
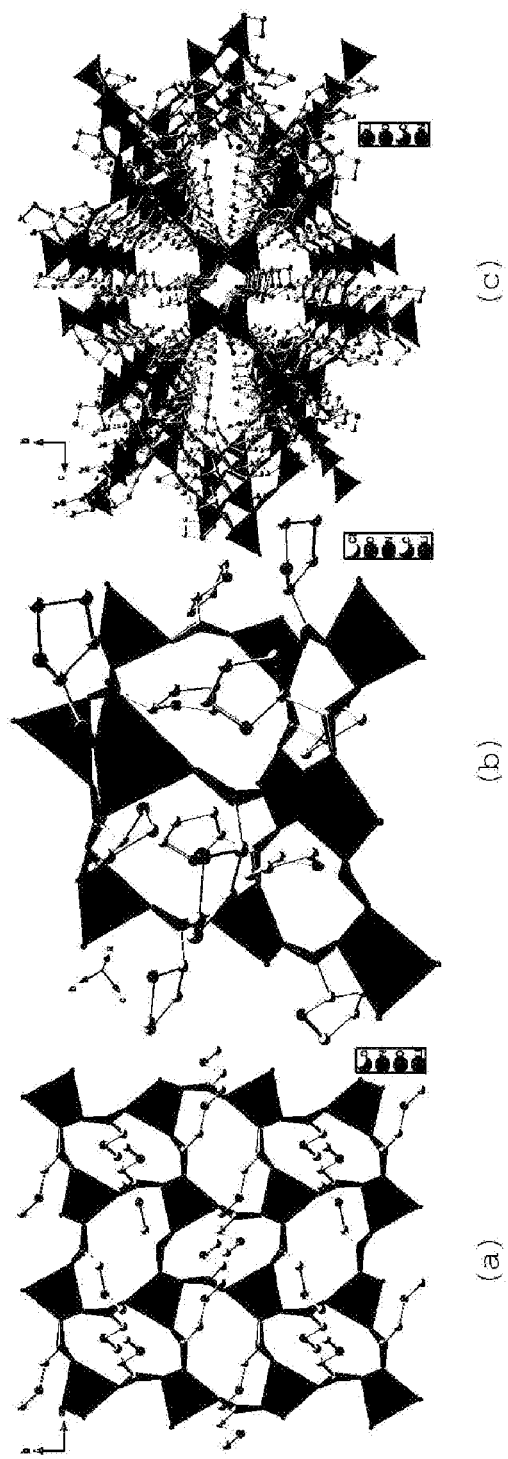
FIG. 2 is a schematic diagram depicting the structural diversity in the networks formed by 2:1 cocrystals of amino acids with lithium salts: (a) square grids; (b) diamondoid LiDMOM nets; (c) zeolitic ABW topology in the first LiZMOM. Hydrogen atoms and counteranions are omitted for clarity.

Square grids exist in LICSAR2 and LINBTN2 as illustrated in FIG. 2(a). Each lithium cation is bridged by four carboxylates [1.905 Å-1.966 Å (LICSAR2) and 1.931 Å-1.973 Å (LINBTN2)] to form an undulating square grid, while the opposite ends of the amino acids point away (above and below) from the square grid to establish a bilayer packing arrangement. The chloride and nitrate anions reside in such an environment that they are surrounded by hydrogen bond donors, N—H•••Cl [3.1011(1)Å, 3.1549(1)Å] and C—H•••O (3.192 Å-3.490 Å] interactions, respectively. These square cavities are ca. 5.0 Å×6.0 Å (LICSAR2) and 5.5×5.7 Å (LINBTN2) and form undulating sheets that stack in a roughly eclipsed manner.

Lithium sustained dia nets, LiDMOMs, are exemplified by LICDMG2, LIBDMG2, LICPRO2, LIBPRO2 and LINPRO2 (dia) as illustrated in FIG. 2(b). Each lithium cation is bridged by four carboxylates [1.898 Å, 1.910 Å (LICDMG2); 1.908 Å, 1.942 Å (LIBDMG2); 1.934 Å, 1.954 Å (LICPRO2); 1.939 Å, 1.974 Å (LIBPRO2); 1.922

Å-1.966 Å (LINPRO2)] to form a cationic dia net with hexagonal channels exhibiting diameters ranging from 10.1 to 12.6 Å. The counterions reside in these channels, the diameters of which are ca. twice that of β-cristobalite (5.9 Å). In each dia net, the framework is reinforced by strong hydrogen bonding [2.742(2), LICDMG2, 2.747(2), LIBDMG2, 2.7404(15), LICPRO2, 2.737(2), LIBPRO2, 2.759 (8), 2.765 (7), LINPRO2] between the carboxylate of one amino acid and the ammonium of an adjacent amino acid. Dia nets are prone to interpenetration but the presence of pairs of counterions and the bulkiness of the amino acid substituents precludes interpenetration in the LiDMOMs reported herein.

Figure 3:
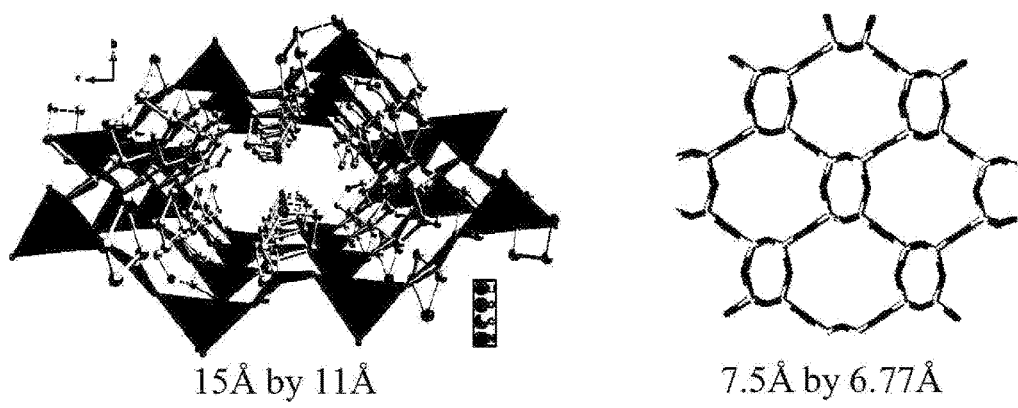
FIG. 3 is a schematic diagram depicting the significant expansion of dimensions that occurs because of the ditopic carboxylate linker in the ABW-type LiZMOM LINPRO2 when compared to prototypal ABW zeolite.

The first example of a lithium sustained zeolitic net, LiZMOM, is a polymorph of LINPRO2 which exists as an ABW net as illustrated in FIG. 2(c). A combination of $Li_4$(carboxylate)$_4$ and $Li_8$(carboxylate)$_8$ rings generate channels that lie parallel to the crystallographic a axis. When viewed down the crystallographic c axis, the presence of $Li_8$(carboxylate)$_8$ rings is evident. Li—O bond distances in the range of 1.913 Å-1.976 Å occur in the 4- and 8-membered rings while Li—O bond distances in the range of 1.920 Å-1.976 Å are observed in the 6-membered rings. Pairs of nitrate anions occupy the 8-membered ring channels and they are crystallographically ordered through N—H•••O hydrogen bonding interactions [2.735(8)Å, 2.885(8)Å, 3.005(8)Å]. The dimensions of the largest 8-membered ring channel are about twice that of an ABW zeolite as illustrated in FIG. 3. ABW topology was reported in one of the first synthetic zeolites as reported by Barrer and White[33] in 1951. They used the term "Li-A" to describe the new structure but the authors' initials were subsequently used when ABW was coined to define this new topology. Although the ABW form of LINPRO2 is stable at elevated temperatures, it converts to the diamondoid form, LINPRO2(dia), upon standing in mother liquor under ambient conditions. Grinding of the plate-like crystals of the LINPRO2(ABW) also results in conversion to LINPRO2(dia) as determined by PXRD. Interestingly, ABW zeolite has been observed as an intermediate phase in inorganic zeolite synthesis.[34]

Whereas the Li-carboxylate bond distances observed in the structures reported herein exhibit a relatively narrow range, the Li-carboxylate-Li angles range from 117.78° ($Li_4$(carboxylate)$_4$ ring in LICSAR2) to 180° [$Li_8$(carboxylate)$_8$ ring in LINPRO2(ABW)] and are detailed in Table 1. The majority of angles cluster around 150°, intermediate between those for linear and tetrahedral geometry, which is consistent with what would be needed to form a wider range of zeolitic structures.

TABLE 1

ANALYSIS OF LI—C—LI ANGLES FORMING 4-, 6- AND 8-MEMBERED RING MOTIFS

| | 4-membered ring motif | 6-membered ring motif | 8-membered ring motif |
|---|---|---|---|
| LICSAR2 | 117.78°, 157.08° | | |
| LINBTN2 | 122.80°, 144.33° | | |
| LICDMG2 | | 153.27° | |
| LIBDMG2 | | 153.27° | |
| LICPRO2 | | 156.00° | |
| LIBPRO2 | | 155.50° | |
| LINPRO2 (dia) | | 154.88°, 158.83° | |
| LINPRO2 (ABW) | 122.13°, 148.72° | 148.72°, 155.18°, 158.97° | 122.13°, 148.72°, 155.18°, 158.97° |
| ABW | 149.4°, 156.8° | 156.8°, 156.9°, 180° | 149.4°, 180° |

As demonstrated herein, 2:1 cocrystals of amino acids with lithium salts generate square grids, diamondoid nets and the first water stable LiZMOM, which exhibits ABW topology. Our approach consists of one-step synthesis from readily available starting materials and should be general because of the modular nature of these compounds and the ready availability of amino acids and counter anions.

Pharmaceutical Forms

Pharmaceutical compositions of the present invention may consist of the active agent, i.e., a composition comprising the lithium salt and a neutral organic compound in a stoichiometric ratio, alone or may include the active agent and any suitable additional component, such as one or more pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Each carrier is preferably acceptable in the sense of being compatible with the other ingredients of the formulation and not injurious to the patient.

Excipients employed in the compositions of the present invention can be solids, semi-solids, liquids or combinations thereof. Preferably, the excipients are solids. Compositions of the invention containing excipients can be prepared by any known technique that comprises, for example, admixing an excipient with the cocrystal. A pharmaceutical composition of the present invention contains a desired amount of the active agent per dose unit and, if intended for oral administration, can be in the form, for example, of a tablet, a caplet, a pill, a hard or soft capsule, a lozenge, a cachet, a dispensable powder, granules, a suspension, an elixir, a dispersion, or any other form reasonably adapted for such administration. If intended for parenteral administration, it can be in the form, for example, of a suspension or transdermal patch. If intended for rectal administration, it can be in the form, for example, of a suppository. Presently preferred are oral dosage forms that are discrete dose units each containing a predetermined amount of the active agent, such as tablets or capsules.

Compositions of the invention optionally comprise one or more pharmaceutically acceptable carriers or diluents as excipients. Suitable carriers or diluents illustratively include, but are not limited to, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of alpha- and amorphous cellulose (e.g., RexcelJ), powdered cellulose, hydroxypropylcellulose (HPC) and hydroxypropylmethylcellulose (HPMC); calcium carbonate; glycine; bentonite; block co-polymers; polyvinylpyrrolidone; and the like. Such carriers or diluents, if present, may constitute in total about 5% to about 99%, about 10% to about 85%, or even about 20% to about 80%, of the total weight of the composition. The carrier, carriers, diluent, or diluents selected may exhibit suitable flow properties and, where tablets are desired, compressibility.

Compositions of the invention optionally comprise one or more pharmaceutically acceptable disintegrants as excipients, particularly for tablet formulations. Suitable disintegrants include, but are not limited to, either individually or in combination, starches, including sodium starch glycolate (e.g., Explotab™ of PenWest) and pregelatinized corn starches (e.g., National™ 1551 of National Starch and Chemical Company, National™ 1550, and Colorcon™ 1500), clays (e.g., Veegum™ HV of R.T. Vanderbilt), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, locust bean, karaya, pectin and tragacanth gums.

Disintegrants may be added at any suitable step during the preparation of the composition, particularly prior to granulation or during a lubrication step prior to compression. Such disintegrants, if present, may constitute in total about 0.2% to about 30%, about 0.2% to about 10%, or even about 0.2% to about 5%, of the total weight of the composition.

Pharmaceutical compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Such binding agents may also prevent or inhibit crystallization or recrystallization of a cocrystal of the present invention once the salt has been dissolved in a solution. Exemplary binding agents and adhesives include, but are not limited to, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™ of Aqualon); and ethylcellulose (e.g., Ethocel™ of the Dow Chemical Company). Such binding agents and/or adhesives, if present, may constitute in total about 0.5% to about 25%, about 0.75% to about 15%, or even about 1% to about 10%, of the total weight of the pharmaceutical composition.

Many of the binding agents are polymers comprising amide, ester, ether, alcohol or ketone groups and, as such, are optionally included in pharmaceutical compositions of the present invention. Exemplary binding agents include polyvinylpyrrolidones such as povidone K-30. Polymeric binding agents can have varying molecular weight, degrees of crosslinking, and grades of polymer. Polymeric binding agents can also be copolymers, such as block co-polymers that contain mixtures of ethylene oxide and propylene oxide units. Variation in these units' ratios in a given polymer affects properties and performance. Examples of block co-polymers with varying compositions of block units are Poloxamer 188 and Poloxamer 237 (BASF Corporation).

Compositions of the invention optionally comprise one or more pharmaceutically acceptable wetting agents as excipients. Such wetting agents may be selected to maintain the cocrystal in close association with water, a condition that may improve bioavailability of the composition. Such wetting agents can also be useful in solubilizing or increasing the solubility of crystals.

Non-limiting examples of surfactants that can be used as wetting agents in compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and degrees Ctoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefosse), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, may constitute in total about 0.25% to about 15%, about 0.4% to about 10%, or even about 0.5% to about 5%, of the total weight of the pharmaceutical composition.

Compositions of the invention optionally comprise one or more pharmaceutically acceptable lubricants (including anti-adherents and/or glidants) as excipients. Exemplary lubricants include, but are not limited to, either individually or in combination, glyceryl behapate (e.g., Compritol™ 888 of Gattefosse); stearic acid and salts thereof, including magnesium, calcium and sodium stearates; hydrogenated vegetable oils (e.g., Sterotex™ of Abitec); colloidal silica; talc; waxes; boric acid; sodium benzoate; sodium acetate; sodium fumarate; sodium chloride; DL-leucine; PEG (e.g., Carbowax™ 4000 and Carbowax™ 6000 of the Dow Chemical Company); sodium oleate; sodium lauryl sulfate; and magnesium lauryl sulfate. Such lubricants, if present, may constitute in total about 0.1% to about 10%, about 0.2% to about 8%, or even about 0.25% to about 5%, of the total weight of the pharmaceutical composition.

The composition may, for example, be a pharmaceutical composition (medicament), a foodstuff, food supplement or beverage. The terms "foodstuff", "food supplement", and "beverage" used herein have the normal meanings for those terms, and are not restricted to pharmaceutical preparations. The appropriate pharmaceutical or edible grade of ingredients will be used, according to the desired composition form.

Pharmaceutical compositions according to the present invention include formulations suitable for oral, rectal, intranasal, topical (including transdermal, buccal and sublingual), vaginal, parental (including subcutaneous, intramuscular, intravenous and intradermal) and pulmonary administration. The formulations can conveniently be presented in unit dosage form and can be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with a suitable carrier, such as liquid carriers or finely divided solid carriers or both, and then if necessary shaping the product. Formulations of the subject invention suitable for oral administration can be presented as discrete units such as capsules, cachets or tablets, each containing a predetermined amount of the active ingredient; or as an oil-in-water liquid emulsion, water-in-oil liquid emulsion, or as a supplement within an aqueous solution, for example, a tea. The active ingredient can also be presented as bolus, electuary, or paste.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; mouthwashes comprising the active ingredient in a suitable liquid carrier; and chocolate comprising the active ingredients.

Formulations suitable for topical administration according to the subject invention can be formulated as an ointment, cream, suspension, lotion, powder, solution, paste, gel, spray, aerosol or oil. Alternatively, a formulation can comprise a patch or a dressing such as a bandage or adhesive plaster impregnated with active ingredients, and optionally one or more excipients or diluents. Topical formulations preferably comprise compounds that facilitate absorption of the active ingredients through the skin and into the bloodstream.

Formulations suitable for intranasal administration, wherein the carrier is a solid, include a coarse powder having a particle size, for example, in the range of about 20 to about 500 microns, which is administered in the manner in which snuff is taken, e.g., by rapid inhalation through the nasal passage from a container of the powder held close up to the nose. Suitable formulations wherein the carrier is a liquid for administration by nebulizer, include aqueous or oily solutions of the agent. Formulations may optionally comprise compounds that facilitate absorption of the active ingredients through the skin and into the bloodstream.

Formulations suitable for parenteral administration include aqueous and non-aqueous isotonic sterile injection solutions which can contain antioxidants, buffers, bacteriostats and solutes which render the formulation isotonic with the blood of the intended recipient; and aqueous and non-aqueous sterile suspensions which can include suspending agents and thickening agents, and liposomes or other microparticulate systems which are designed to target the compound to blood components or one or more organs. The formulations can be presented in unit-dose or multi-dose or multi-dose sealed containers, such as for example, ampoules and vials, and can be stored in a freeze-dried (lyophilized) condition requiring only the addition of the sterile liquid carrier, for example, water for injections, immediately prior to use. Extemporaneous injection solutions and suspensions can be prepared from sterile powders, granules and tablets of the kind previously described.

It should be understood that in addition to the ingredients particularly mentioned above, the formulations useful in the present invention can include other agents conventional in the art regarding the type of formulation in question. For example, formulations suitable for oral administration can include such further agents as sweeteners, thickeners, and flavoring agents. It also is intended that the agents, compositions, and methods of this invention be combined with other suitable compositions and therapies.

Various delivery systems are known in the art and can be used to administer a therapeutic agent or composition of the invention, e.g., encapsulation in liposomes, microparticles, microcapsules, receptor-mediated endocytosis and the like. Methods of administration include, but are not limited to, parenteral, intra-arterial, intramuscular, intravenous, intranasal, and oral routes. The pharmaceutical compositions can be provided in the form of tablets, lozenges, granules, capsules, pills, ampoule, suppositories or aerosol form. The pharmaceutical compositions can also be provided in the form of suspensions, solutions, and emulsions of the active ingredient in aqueous or non-aqueous diluents, syrups, granulates or powders.

Pharmaceutical formulations of the invention can be administered simultaneously or sequentially with other drugs or biologically active agents. Examples include, but are not limited to, antioxidants, free radical scavenging agents, peptides, growth factors, antibiotics, bacteriostatic agents, immunosuppressives, anticoagulants, buffering agents, anti-inflammatory agents, anti-pyretics, time-release binders, anesthetics, steroids and corticosteroids.

Preferred unit dosage formulations are those containing a daily dose or unit, daily subdose, or an appropriate fraction thereof, of an agent. Therapeutic amounts can be empirically determined and will vary with the condition being treated, the subject being treated, and the efficacy and toxicity of the agent. Similarly, suitable dosage formulations and methods of administering the agents can be readily determined by those of ordinary skill in the art.

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

LINPRO2-Forms I & II 1:2 Cocrystal of LiNO$_3$ and L-Proline

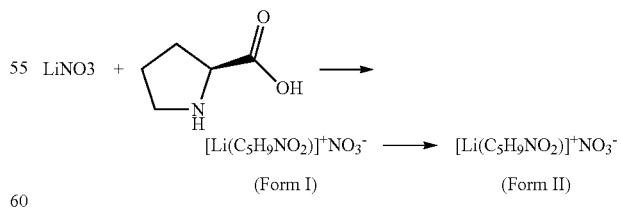

Lithium nitrate (98%, anhydrous, used as received from Fluka, 413.4 mg, 6.0 mmol) and L-proline (99-F % pure, used as received from Acros Organics, 1381.2 mg, 12.0 mmol) were dissolved in 2.0 ml of hot deionised water. It was maintained on the hot plate until crystals emerged from the hot solution. Colorless plates (Form I, metastable form)

were collected from the hot solution which in due course of time transform to 3-D rhombohedral crystals (Form II, 603 mg) once they are removed from the hot plate.

Melting point=176.1° C. (Form II).

Crystals of LINPRO2 Forms I and II were characterized by single crystal X-ray crystallography (Tables 1a and 1b). LINPRO2, Form II, crystals were also analyzed by FT-IR spectroscopy, DSC, TGA, and powder X-ray diffraction.

The single crystal x-ray structural analysis reveals that LINPRO2, Form I (metastable form), contains two lithium cations, two nitrate anions and four L-proline molecules in the asymmetric unit. Each lithium is coordinated by four bridging carboxylate and the overall structure results in the formation of zeolite ABW framework. LINPRO2, Form II, contains one lithium cation, one nitrate anion and two L-proline molecules in the asymmetric unit. Each lithium is coordinated by four bridging carboxylate and the overall structure results in the formation of diamondoid network. In both the forms the ammonium cations ($R_2NH_2^+$) hydrogen bond to the nitrate anions and a hydrogen bond to an adjacent carboxylate.

TABLE 1a

Single crystal X-ray diffraction data for LINPRO2-Form I (Bruker-AXS APEX2 CCD diffractometer) Crystallographic data

| | |
|---|---|
| Empirical formula | $C_{10}H_{18}N_3O_7Li$ |
| Formula weight | 299.21 |
| Temperature | 100 (2) K |
| Wavelength | 1.54178 Å |
| Crystal system | Orthorhombic |
| Space group | $P2_12_12_1$ |
| Unit cell dimensions | a = 11.0448(3) Å  α = 90° |
| | b = 12.0393(3) Å  β = 90° |
| | c = 20.2019(5) Å  γ = 90° |
| Volume | 2687.34 Å$^3$ |
| Z | 8 |
| Density (calculated) | 1.480 Mg/m$^3$ |
| Reflections collected | 15510 |
| Independent reflections | 4505 [R(int) = 0.0458] |
| Final R indices [I > 2sigma(I)] | R1 = 0.0314, wR2 = 0.0799 |
| R indices (all data) | R1 = 0.0337, wR2 = 0.0812 |

TABLE 1b

Single crystal X-ray diffraction data for LINPRO2-Form II (Bruker-AXS APEX2 CCD diffractometer) Crystallographic data

| | |
|---|---|
| Empirical formula | $C_{10}H_{18}N_3O_7Li$ |
| Formula weight | 299.21 |
| Temperature | 100 (2) K |
| Wavelength | 1.54178 Å |
| Crystal system | Orthorhombic |
| Space group | $P2_12_12_1$ |
| Unit cell dimensions | a = 9.4746 (5) Å  α = 90° |
| | b = 9.5817 (5) Å  β = 90° |
| | c = 15.0372 (7) Å  γ = 90° |
| Volume | 1362.97 Å$^3$ |
| Z | 4 |
| Density (calculated) | 1.456 Mg/m$^3$ |
| Reflections collected | 9047 |
| Independent reflections | 2308 [R(int) = 0.0545] |
| Final R indices [I > 2sigma(I)] | R1 = 0.1164, wR2 = 0.3273 |
| R indices (all data) | R1 = 0.1177, wR2 = 0.3279 |

Example 2

LIBPRO

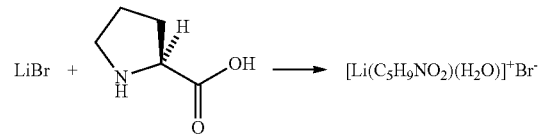

Lithium bromide, anhydrous (99% pure, used as received from Acros Organics, 1 g, 11.5 mmol) and L-proline (99-F % pure, used as received from Aldrich, 1.33 g, 11.5 mmol) were dissolved in 2.0 ml of hot deionised water. It was maintained on the hot plate until crystals emerged from the hot solution. Colourless block crystals (1427 mg) were harvested from the hot solution. Crystals of LIBPRO were characterized by FT-IR spectroscopy, DSC, TGA, powder x-ray diffraction and single crystal x-ray crystallography (Table 2).

Melting point=280° C.

The single crystal x-ray structural analysis reveals that LIBPRO contains four lithium cations, four bromide anions, four L-proline molecules and four water molecules in the unit cell. Three carboxylates bridge one lithium cations to form a chain of fused six-membered rings. The tetrahedral coordination environment of the lithium cations were achieved by three bridging carboxylates and a water molecule. The bromide anion acts as hydrogen bond acceptors towards two water molecules and two ammonium groups.

TABLE 2

Single crystal x-ray diffraction data for LIBPRO (Bruker-AXS APEX2 CCD diffractometer) Crystallographic data

| | |
|---|---|
| Empirical formula | $[Li(C_5H_9NO_2)(H_2O)]^+Br^-$ |
| Formula weight | 220.00 |
| Temperature | 100(2) K |
| Wavelength | 1.54178 Å |
| Crystal system | Monoclinic |
| Space group | $P2_1$ |
| Unit cell dimensions | a = 11.2473(3) Å  α = 90° |
| | b = 5.13160(10) Å  β = 104.3950(10)° |
| | c = 14.9547(4) Å  γ = 90° |
| Volume | 836.04(4) Å$^3$ |
| Z | 4 |
| Density (calculated) | 1.748 Mg/m$^3$ |
| Reflections collected | 7150 |
| Independent reflections | 2675 [R(int) = 0.0266] |
| Final R indices [I > 2sigma(I)] | R1 = 0.0200, wR2 = 0.0502 |
| R indices (all data) | R1 = 0.0201, wR2 = 0.0503 |

Example 3

LIBPRO2

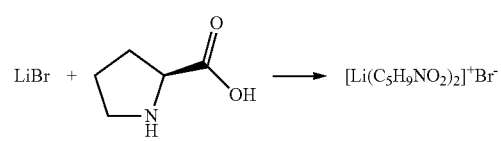

Lithium bromide (99+%, anhydrous, used as received from Acros Organics, 0.50 g, 5.76 mmol) and L-proline (99-F % pure, used as received from Acros Organics, 1.33 g, 11.5 mmol) were dissolved in 2.0 ml of hot deionised water. It was maintained on the hot plate until crystals emerged from the hot solution. Colourless block crystals (861 mg) were collected from the hot solution. Crystals of LIBPRO2 were characterized by FT-IR spectroscopy, DSC, TGA, powder x-ray diffraction and single crystal x-ray crystallography (Table 3).

Melting point=257° C.

The single crystal x-ray structural analysis reveals that LIBPRO2 contains four lithium cations, four chloride anions and eight L-proline molecules in the unit cell. Each lithium cation is bridged by four carboxylates to form a cationic dia net with hexagonal channels exhibiting diameters ranging from 10.2 Å to 12.6 Å, populated by the bromide anions. The framework is reinforced by hydrogen bonding between the carboxylate of one amino acid and the ammonium of an adjacent amino acid [N—H•••O, 2.737(2) Å]. The presence of pairs of bromide anions [N—H•••Br, 3.2769(15) Å] in these hexagonal channels interacting with neighbouring ammonium groups renders interpenetration impossible.

TABLE 3

Single crystal x-ray diffraction data for LIBPRO2
(Bruker-AXS APEX2 CCD diffractometer)
Crystallographic data

| Empirical formula | $[Li(C_5H_9NO_2)_2]^+Br^-$ | |
|---|---|---|
| Formula weight | 317.11 | |
| Temperature | 100(2) K | |
| Wavelength | 1.54178 Å | |
| Crystal system | Tetragonal | |
| Space group | $P4_12_12$ | |
| Unit cell dimensions | a = 9.1703(3) Å | $\alpha = 90°$ |
| | b = 9.1703(3) Å | $\beta = 90°$ |
| | c = 15.5694(14) Å | $\gamma = 90°$ |
| Volume | 1309.30(13) Å$^3$ | |
| Z | 4 | |
| Density (calculated) | 1.609 Mg/m$^3$ | |
| Reflections collected | 11372 | |
| Independent reflections | 1182 [R(int) = 0.0429] | |
| Final R indices | R1 = 0.0181, wR2 = 0.0447 | |
| [I > 2sigma(I)] | | |
| R indices (all data) | R1 = 0.0185, wR2 = 0.0449 | |

Example 4

LIBDMG2

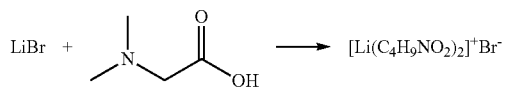

Lithium bromide (99%, anhydrous, used as received from Acros Organics, 0.5 g, 5.76 mmol) and N,N-dimethylglycine (used as received from Alfa Aesar, 1.19 g, 11.5 mmol) were dissolved in 2.0 ml of hot deionised water. It was maintained on the hot plate until crystals emerged from the hot solution. Colourless block crystals (696 mg) were collected from the hot solution. Crystals of LIBDMG2 were characterized by FT-IR spectroscopy, DSC, TGA, powder x-ray diffraction and single crystal x-ray crystallography (Table 4).

Melting point=289° C.

The single crystal x-ray structural analysis reveals that LIBDMG2 contains eight lithium cations, eight bromide anions and sixteen N,N-dimethylglycine molecules in the unit cell. Each lithium cation is bridged by four carboxylates to form a cationic diamondoid net with hexagonal channels exhibiting diameters ranging from 10.7 Å to 12.1 Å, populated by the bromide anions. The framework is reinforced by hydrogen bonding between the carboxylate of one amino acid and the ammonium of an adjacent amino acid [N—H•••O, 2.747(2) Å]. The presence of pairs of bromide anions [C—H•••Br, 3.717 Å, 3.731 Å and 3.772 Å] in these hexagonal channels interacting with neighboring methyl groups renders interpenetration impossible.

TABLE 4

Single crystal x-ray diffraction data for LIBDMG2
(Bruker-AXS APEX2 CCD diffractometer)
Crystallographic data

| Empirical formula | $[Li(C_4H_9NO_2)_2]^+Br^-$ | |
|---|---|---|
| Formula weight | 293.09 | |
| Temperature | 100(2) K | |
| Wavelength | 1.54178 Å | |
| Crystal system | Orthorhombic | |
| Space group | Fdd2 | |
| Unit cell dimensions | a = 14.0912(2) Å | $\alpha = 90°$ |
| | b = 14.9035(2) Å | $\beta = 90°$ |
| | c = 12.5426(2) Å | $\gamma = 90°$ |
| Volume | 2634.05(7) Å$^3$ | |
| Z | 8 | |
| Density (calculated) | 1.478 Mg/m$^3$ | |
| Reflections collected | 5081 | |
| Independent reflections | 1114 [R(int) = 0.0335] | |
| Final R indices | R1 = 0.0178, wR2 = 0.0464 | |
| [I > 2sigma(I)] | | |
| R indices (all data) | R1 = 0.0180, wR2 = 0.0465 | |

Example 5

LINSER2

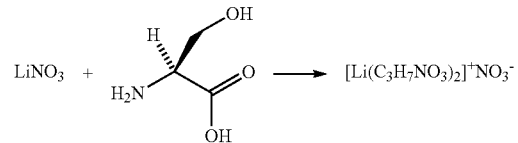

Lithium nitrate (99%, anhydrous, used as received from Acros Organics, 414 mg, 6.0 mmol) and L-Serine (used as received from Acros Organics, 635.4 mg, 6.0 mmol) were dissolved in 3.0 mL of hot deionised water. It was maintained on the hot plate until crystals emerged from the hot solution. Colorless rods were collected from the hot solution. Crystals of LINSER2 were characterized by FT-IR spectroscopy, DSC, TGA, powder x-ray diffraction, and single crystal X-ray crystallography (Table 5).

Melting point=204° C.

The single crystal X-ray structural analysis reveals that LINSER2 is a 1:2 cocrystal of lithium nitrate and L-serine. Each lithium cation is bridged by four carboxylates to form an undulating square grid. Each ammonium cation (R$_3$NH$^+$) form hydrogen bonds to the O—H functionalities of two adjacent L-serine molecules and a nitrate anion.

TABLE 5

Single crystal x-ray diffraction data for LINSER2
(Bruker-AXS APEX2 CCD diffractometer)
Crystallographic data

| | |
|---|---|
| Empirical formula | [Li(C$_3$H$_7$NO$_3$)$_2$]$^+$NO$_3^-$ |
| Formula weight | 279.14 |
| Temperature | 100(2) K |
| Wavelength | 1.54178 Å |
| Crystal system | Orthorhombic |
| Space group | P2$_1$2$_1$2$_1$ |
| Unit cell dimensions | a = 4.8395(4) Å   α = 90° |
| | b = 8.7210(6) Å   β = 90° |
| | c = 26.4305(18) Å   γ = 90° |
| Volume | 1115.51(14) Å$^3$ |
| Z | 4 |
| Density (calculated) | 1.662 Mg/m$^3$ |
| Reflections collected | 8996 |
| Independent reflections | 1950 [R(int) = 0.0317] |
| Final R indices [I > 2sigma(I)] | R1 = 0.0326, wR2 = 0.1071 |
| R indices (all data) | R1 = 0.0392, wR2 = 0.1392 |

Example 6

LINPRO

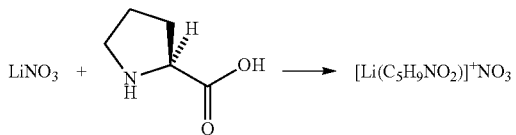

Lithium nitrate (98%, anhydrous, used as received from Fluka, 413.4 mg, 6.0 mmol) and L-proline (99+% pure, used as received from Aldrich, 690.0 mg, 0.599 mmol) were dissolved in 1.5 mL of deionised water and was maintained on the hot plate until crystals emerged from the hot solution. Colorless plates (473.8 mg) were collected from the hot solution and used for further analysis. Crystals of LINPRO were characterized by FT-IR spectroscopy, DSC, TGA, powder X-ray diffraction and single crystal X-ray crystallography (Table 6).

Melting point=232° C.

The single crystal X-ray structural analysis reveals that LINPRO is a 1:1 cocrystal. Each lithium cation is bridged by two carboxylates and two nitrates anions to form a diamondoid network. Each ammonium group of L-proline hydrogen bonds to one carboxylate and the nitrate anion.

TABLE 6

Single crystal X-ray diffraction data for LINPRO
(Bruker-AXS APEX2 CCD diffractometer)
Crystallographic data

| | |
|---|---|
| Empirical formula | [Li(C$_5$H$_9$NO$_2$)]$^+$NO3$^-$ |
| Formula weight | 184.08 |
| Temperature | 100(2) K |
| Wavelength | 1.54178 Å |
| Crystal system | Orthorhombic |
| Space group | P2$_1$2$_1$2$_1$ |
| Unit cell dimensions | a = 9.0947(4) Å   α = 90° |
| | b = 9.2876(5) Å   β = 90° |
| | c = 9.5743(5) Å   γ = 90° |
| Volume | 808.72 (7) Å$^3$ |
| Z | 4 |
| Density (calculated) | 1.512 Mg/m$^3$ |
| Reflections collected | 6265 |

TABLE 6-continued

Single crystal X-ray diffraction data for LINPRO
(Bruker-AXS APEX2 CCD diffractometer)
Crystallographic data

| | |
|---|---|
| Independent reflections | 1406 [R(int) = 0.0557] |
| Final R indices [I > 2sigma(I)] | R1 = 0.0290, wR2 = 0.0739 |
| R indices (all data) | R1 = 0.0302, wR2 = 0.0745 |

Example 7

LINPRO2-Form I

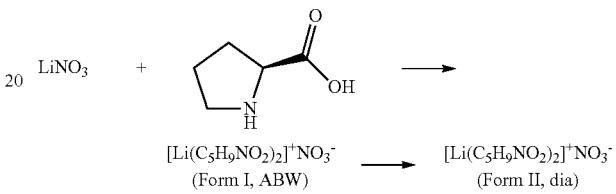

Lithium nitrate (98%, anhydrous, used as received from Fluka, 413.4 mg, 6.0 mmol) and L-proline (99+% pure, used as received from Acros Organics, 1381.2 mg, 12.0 mmol) were dissolved in 2.0 ml of hot deionised water. It was maintained on the hot plate until crystals emerged from the hot solution. Colorless plates (Form I, ABW, metastable form) were collected from the hot solution which in due course of time transform to 3-D rhombohedral crystals (Form II, dia, 603 mg) once they are removed from the hot plate. Crystals of LINPRO2 Forms I and II were characterized by single crystal X-ray crystallography. LINPRO2 (Form II, dia) crystals were also analyzed by FT-IR spectroscopy, DSC, TGA powder X-ray diffraction.

Melting point=2176° C. (Form II, dia.)

The single crystal x-ray structural analysis reveals LINPRO2 (Form II, dia) contains one lithium cation, one nitrate anion and two L-proline molecules in the asymmetric unit. Each lithium cation is bridged by four carboxylates to form a cationic diamondoid net with hexagonal channels exhibiting diameters ranging from 10.6 Å to 12.3 Å, populated by the nitrate anions. The framework is reinforced by hydrogen bonding between the carboxylate of one amino acid and the ammonium of an adjacent amino acid [N—H•••O, 2.759(8) Å, 2.765 (7) Å]. The presence of pairs of nitrate anions [N—H•••O, 2.735(8) Å, 2.885(8) Å, 3.005(8) Å] in these hexagonal channels interacting with neighboring ammonium groups renders interpenetration impossible. LINPRO2 (Form I, ABW, metastable form) exhibits a combination of 4- and 8-membered ring channels down the crystallographic a axis. When viewed down the crystallographic c axis, 6-membered ring channels are observed. Here, pairs of nitrate anions occupy the 8-membered ring channels, aided by N—H•••O interactions [2.735(8) Å, 2.885(8) Å, 3.005(8) Å].

TABLE 7

Single crystal X-ray diffraction data for LINPRO2-
Form I (Bruker-AXS APEX2 CCD diffractometer)
Crystallographic data

| | |
|---|---|
| Empirical formula | [Li(C$_5$H$_9$NO$_2$)$_2$]$^+$NO$_3^-$ |
| Formula weight | 299.21 |

TABLE 7-continued

Single crystal X-ray diffraction data for LINPRO2-
Form I (Bruker-AXS APEX2 CCD diffractometer)
Crystallographic data

| Temperature | 100 (2) K | |
|---|---|---|
| Wavelength | 1.54178 Å | |
| Crystal system | Orthorhombic | |
| Space group | P2$_1$2$_1$2$_1$ | |
| Unit cell dimensions | a = 11.0448(3) Å | α = 90° |
| | b = 12.0393(3) Å | β = 90° |
| | c = 20.2019(5) Å | γ = 90° |
| Volume | 2686.28(12) Å$^3$ | |
| Z | 8 | |
| Density (calculated) | 1.480 Mg/m$^3$ | |
| Reflections collected | 15510 | |
| Independent reflections | 4505 [R(int) = 0.0458] | |
| Final R indices [I > 2sigma(I)] | R1 = 0.0314, wR2 = 0.0799 | |
| R indices (all data) | R1 = 0.0337, wR2 = 0.0812 | |

Example 8

LINSAR

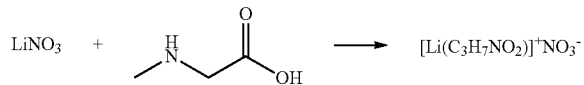

Lithium nitrate (98%, anhydrous, used as received from Fluka, 413.4 mg, 6.0 mmol) and sarcosine (98% pure, used as received from Aldrich, 534.5 mg, 6.0 mmol) were dissolved in 1 mL of deionised water. It was maintained on the hot plate until crystals emerged from the hot solution. Colorless crystals (368.4 mg) were collected from the hot solution and used for further analysis. Crystals of LINSAR were characterized by FT-IR spectroscopy, DSC, TGA, powder x-ray diffraction, and single crystal X-ray crystallography (Table 8).

Melting point=208° C.

The single crystal x-ray structural analysis reveals that LINSAR contains four formula units in the unit cell. Three carboxylates bridge two lithium cations to form a chain of fused six-membered ring. The tetrahedral coordination environment of the lithium cations were achieved by three bridging carboxylates and one nitrate anion. Each ammonium group (R$_2$NH$_2$$^+$) forms two hydrogen bonds to two nitrate anions.

TABLE 8

Single crystal X-ray diffraction data for LINSAR
(Bruker-AXS APEX2 CCD diffractometer)
Crystallographic data

| Empirical formula | [Li(C$_3$H$_7$NO$_2$)]$^+$NO$_3$$^-$ | |
|---|---|---|
| Formula weight | 158.05 | |
| Temperature | 293(2) K | |
| Wavelength | 1.54178 Å | |
| Crystal system | Orthorhombic | |
| Space group | P2$_1$2$_1$2$_1$ | |
| Unit cell dimensions | a = 5.0816(5) Å | α = 90° |
| | b = 10.7057(9) Å | β = 90° |
| | c = 12.5344(10) Å | γ = 90° |
| Volume | 681.90(10) Å$^3$ | |
| Z | 4 | |
| Density (calculated) | 1.539 Mg/m$^3$ | |
| Reflections collected | 3048 | |

TABLE 8-continued

Single crystal X-ray diffraction data for LINSAR
(Bruker-AXS APEX2 CCD diffractometer)
Crystallographic data

| Independent reflections | 1153 [R(int) = 0.0347] |
|---|---|
| Final R indices [I > 2sigma(I)] | R1 = 0.0384, wR2 = 0.1079 |
| R indices (all data) | R1 = 0.0439, wR2 = 0.1125 |

Example 9

LININA

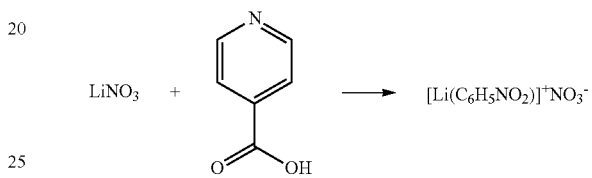

Lithium nitrate (98%, anhydrous, used as received from Fluka, 413.4 mg, 6.0 mmol) and isonicotinic acid (98% pure, used as received from Aldrich, 40 mg, 0.325 mmol) were dissolved in 3 mL of deionised water. It was maintained on the hot plate until crystals emerged from the hot solution. Colorless plates (368.4 mg) were collected from the hot solution and used for further analysis. Crystals of LININA were characterized by FT-IR spectroscopy, DSC, TGA, powder x-ray diffraction, and single crystal X-ray crystallography (Table 9).

Melting point=208° C.

The single crystal X-ray structural analysis reveals that LININA is a 1:1 cocrystal of LiNO$_3$ and isonicotinic acid. The tetrahedral coordination environment of the lithium cations were achieved by three bridging carboxylates and the nitrate anions. Each nitrate anion forms bifurcated hydrogen bonds to ammonium cations (R$_2$NH$_2$$^+$) and to the neighboring nitrate anions.

TABLE 9

Single crystal X-ray diffraction data for LININA
(Bruker-AXS APEX2 CCD diffractometer)
Crystallographic data

| Empirical formula | [Li(C$_6$H$_5$NO$_2$)]$^+$NO$_3$$^-$ | |
|---|---|---|
| Formula weight | 192.06 | |
| Temperature | 293(2) K | |
| Wavelength | 1.54178 Å | |
| Crystal system | Monoclinic | |
| Space group | P2$_1$/c | |
| Unit cell dimensions | a = 9.9315(6) Å | α = 90° |
| | b = 10.0382(6) Å | β = 91.201(4)° |
| | c = 7.5846(5) Å | γ = 90° |
| Volume | 755.98(8) Å$^3$ | |
| Z | 4 | |
| Density (calculated) | 1.687 Mg/m$^3$ | |
| Reflections collected | 5981 | |
| Independent reflections | 1250 [R(int) = 0.0692] | |
| Final R indices [I > 2sigma(I)] | R1 = 0.0436, wR2 = 0.1097 | |
| R indices (all data) | R1 = 0.0542, wR2 = 0.1183 | |

Example 10

LINDMG

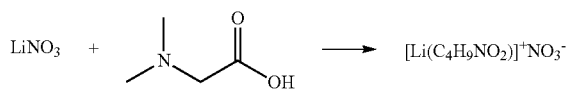

Lithium nitrate (98%, anhydrous, used as received from Fluka, 413.4 mg, 6.0 mmol) and N,N-dimethylglycine (used as received from Alfa Aesar, 618 mg, 6.0 mmol) were dissolved in 3.0 mL of hot deionised water. It was maintained on the hot plate until crystals emerged from the hot solution. Colorless plates (595 mg) were collected from the hot solution. Crystals of LINDMG were characterized by FT-IR spectroscopy, DSC, TGA, powder X-ray diffraction, and single crystal X-ray crystallography (Table 10).

Melting point=202° C.

The single crystal X-ray structural analysis reveals that LINDMG is a 1:1 cocrystal with each lithium cation, nitrate anion and dimethylglycine molecule in the asymmetric unit. Three carboxylates bridge one lithium cation to form a chain of fused six-membered ring. Each lithium cation is coordinated to three carboxylates and one nitrate anion which fulfills the tetrahedral environment of lithium. The nitrate anions hydrogen bonds to the ammonium group of the dimethylglycine molecules.

TABLE 10

Single crystal x-ray diffraction data for LINDMG
(Bruker-AXS APEX2 CCD diffractometer)
Crystallographic data

| | |
|---|---|
| Empirical formula | [Li(C$_4$H$_9$NO$_2$)]$^+$NO$_3^-$ |
| Formula weight | 172.07 |
| Temperature | 100(2) K |
| Wavelength | 1.54178 Å |
| Crystal system | Orthorhombic |
| Space group | Fdd2 |
| Unit cell dimensions | a = 21.7388(6) Å  α = 90° |
| | b = 29.0098(8) Å  β = 90° |
| | c = 4.9930(2) Å  γ = 90° |
| Volume | 3148.78(18) Å$^3$ |
| Z | 16 |
| Density (calculated) | 1.452 Mg/m$^3$ |
| Reflections collected | 5895 |
| Independent reflections | 1190 [R(int) = 0.0313] |
| Final R indices [I > 2sigma(I)] | R1 = 0.0269, wR2 = 0.0812 |
| R indices (all data) | R1 = 0.0282, wR2 = 0.0827 |

Example 11

LINBTN2

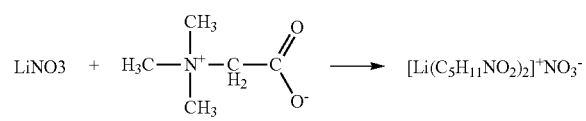

Lithium nitrate (98%, anhydrous, used as received from Fluka, 413.4 mg, 6.0 mmol) and betaine (99+% pure, used as received from Sigma, 1405.6 mg, 12.0 mmol) were dissolved in 2.0 mL of hot deionised water. It was maintained on the hot plate until crystals emerged from the hot solution. Colorless plates (357 mg) were collected from the hot solution and used for further analysis. Crystals of LINBTN2 were characterized by FT-IR spectroscopy, DSC, TGA, powder X-ray diffraction, and single crystal X-ray crystallography (Table 11).

Melting point=286° C.

The single crystal x-ray structural analysis reveals that LINBTN2 crystallizes out in monoclinic space group with one lithium cation, one nitrate anion and two betaine molecules in the asymmetric unit. Each lithium cation is bridged by four carboxylates to form an undulating square grid, while the opposite ends of the amino acids point away (above and below) from the square grid to establish a bilayer packing arrangement. The nitrate anions reside at the interface of the ammonium groups, sustained by C—H•••O (ranging from 3.385 Å to 3.607 Å) interactions. These square cavities are about 5.5 Å by 5.7 Å.

TABLE 11

Single crystal x-ray diffraction data for LINBTN2
(Bruker-AXS APEX2 CCD diffractometer)
Crystallographic data

| | |
|---|---|
| Empirical formula | [Li(C$_5$H$_{11}$NO$_2$)$_2$]$^+$NO$_3^-$ |
| Formula weight | 303.25 |
| Temperature | 100 (2) K |
| Wavelength | 1.54178 Å |
| Crystal system | Monoclinic |
| Space group | P2$_1$/c |
| Unit cell dimensions | a = 16.047(2) Å  α = 90° |
| | b = 8.477(1) Å  β = 103.731 (6)° |
| | c = 10.884(1) Å  γ = 90° |
| Volume | 1438.2(3) Å$^3$ |
| Z | 4 |
| Density (calculated) | 1.401 Mg/m$^3$ |
| Reflections collected | 8654 |
| Independent reflections | 2460 [R(int) = 0.0295] |
| Final R indices [I > 2sigma(I)] | R1 = 0.0422, wR2 = 0.1160 |
| R indices (all data) | R1 = 0.0490, wR2 = 0.1222 |

Example 12

LICSAR

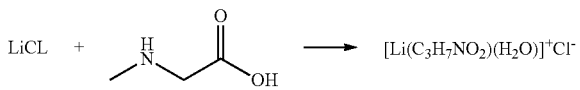

Lithium chloride, anhydrous (99% pure, used as received from Acros Organics, 100.0 mg, 2.36 mmol) and sarcosine (98% pure, used as received from Aldrich, 211.0 mg, 2.36 mmol) were dissolved in 0.5 ml of deionised water and left for slow evaporation. Colourless plate-like crystals (200 mg) were harvested after three days.

Melting point=245° C.

Crystals of LICSAR were characterized by FT-IR spectroscopy, DSC, TGA, powder x-ray diffraction, single crystal x-ray crystallography (Table 12) and the dissolution profile in water.

The single crystal x-ray structural analysis reveals that LICSAR contains four lithium cations, four chloride anions, four sarcosine molecules and four water molecules in the unit cell. Three carboxylates bridge one lithium cation to form a chain of fused six-membered ring. The tetrahedral coordination environment of the lithium cations were achieved by three bridging carboxylates and a water molecule. Each ammonium group ($R_2NH_2^+$) forms two hydrogen bonds to two chloride anions.

TABLE 12

Single crystal x-ray diffraction data for LICSAR
(Bruker-AXS APEX2 CCD diffractometer)
Crystallographic data

| | |
|---|---|
| Empirical formula | $[Li(C_3H_7NO_2)(H_2O)]^+Cl^-$ |
| Formula weight | 149.5 |
| Temperature | 100(2) K |
| Wavelength | 1.54178 Å |
| Crystal system | Orthorhombic |
| Space group | $P2_12_12_1$ |
| Unit cell dimensions | a = 4.9169(2) Å   α = 90° |
| | b = 5.2917(2) Å   β = 90° |
| | c = 27.9380(10) Å   γ = 90° |
| Volume | 726.91(5) Å$^3$ |
| Z | 4 |
| Density (calculated) | 1.366 Mg/m$^3$ |
| Reflections collected | 6032 |
| Independent reflections | 1288 [R(int) = 0.0552] |
| Final R indices [I > 2sigma(I)] | R1 = 0.0671, wR2 = 0.1581 |
| R indices (all data) | R1 = 0.0708, wR2 = 0.1601 |

Example 13

LICSAR2

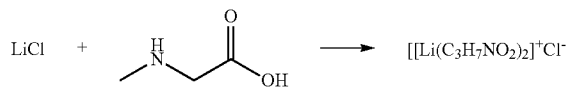

Lithium chloride, anhydrous (99% pure, used as received from Acros Organics, 0.5 g, 11.8 mmol) and sarcosine (98% pure, used as received from Aldrich, 3.15 g, 35.4 mmol) were dissolved in 2 ml of hot deionised water. It was maintained on the hot plate until crystals emerged from the solution. Colourless block crystals (1213 mg) were harvested from the hot solution.

Melting point=247° C.

Crystals of LICSAR2 were characterized by FT-IR spectroscopy, DSC, TGA, powder x-ray diffraction, and single crystal x-ray crystallography (Table 13).

The single crystal x-ray structural analysis reveals that LICSAR2 contains eight lithium cations, eight chloride anions, sixteen sarcosine molecules in the unit cell. Each lithium cation is bridged by four carboxylates to form an undulating square grid, while the opposite ends of the amino acids point away (above and below) from the square grid to establish a bilayer packing arrangement. The chloride anions reside at the interface of the ammonium groups, sustained by N—H•••Cl [3.1011(1) Å, 3.1549(1) Å] interactions. These square cavities are about 5.0 Å by 6.0 Å.

TABLE 13

Single crystal x-ray diffraction data for LICSAR2
(Bruker-AXS APEX2 CCD diffractometer)
Crystallographic data

| | |
|---|---|
| Empirical formula | $[Li(C_3H_7NO_2)_2]^+Cl^-$ |
| Formula weight | 220.58 |
| Temperature | 100(2) K |
| Wavelength | 1.54178 Å |
| Crystal system | Orthorhombic |

TABLE 13-continued

Single crystal x-ray diffraction data for LICSAR2
(Bruker-AXS APEX2 CCD diffractometer)
Crystallographic data

| | |
|---|---|
| Space group | Pbca |
| Unit cell dimensions | a = 9.5197(1) Å   α = 90° |
| | b = 9.9275(1) Å   β = 90° |
| | c = 21.7783(2) Å   γ = 90° |
| Volume | 2058.20(4) Å$^3$ |
| Z | 8 |
| Density (calculated) | 1.424 Mg/m$^3$ |
| Reflections collected | 16164 |
| Independent reflections | 1838 [R(int) = 0.0407] |
| Final R indices [I > 2sigma(I)] | R1 = 0.0274, wR2 = 0.0786 |
| R indices (all data) | R1 = 0.0290, wR2 = 0.0798 |

Example 14

LICPRO

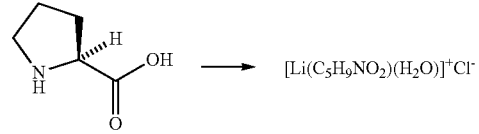

Lithium chloride, anhydrous (99% pure, used as received from Acros Organics, 200.0 mg, 4.72 mmol) and L-proline (99+% pure, used as received from Aldrich, 544.0 mg, 4.72 mmol) were dissolved in 0.75 ml of deionised water and left for slow evaporation. Colourless plate crystals (609 mg) were harvested after three days.

Melting point=281° C.

Crystals of LICPRO were characterized by FT-IR spectroscopy, DSC, TGA, powder x-ray diffraction, single crystal x-ray crystallography (Table 14) and the dissolution profile in water. The single crystal x-ray structural analysis reveals that LICPRO contains two lithium cations, two chloride anions, two L-proline molecules and two water molecules in the unit cell. Three carboxylates bridge one lithium cations to form a chain of fused six-membered rings. The tetrahedral coordination environment of the lithium cations were achieved by three bridging carboxylates and a water molecule. The chloride anion acts as hydrogen bond acceptors towards two water molecules and two ammonium groups.

The single crystal x-ray structural analysis reveals that LICPRO contains two lithium cations, two chloride anions, two L-proline molecules and two water molecules in the unit cell. Three carboxylates bridge one lithium cations to form a chain of fused six-membered rings. The tetrahedral coordination environment of the lithium cations were achieved by three bridging carboxylates and a water molecule. The chloride anion acts as hydrogen bond acceptors towards two water molecules and two ammonium groups.

TABLE 14

Single crystal x-ray diffraction data for LICPRO
(Bruker-AXS APEX2 CCD diffractometer)
Crystallographic data

| | |
|---|---|
| Empirical formula | $[Li(C_5H_9NO_2)(H_2O)]^+Cl^-$ |
| Formula weight | 175.54 |
| Temperature | 100(2) K |

TABLE 14-continued

Single crystal x-ray diffraction data for LICPRO
(Bruker-AXS APEX2 CCD diffractometer)
Crystallographic data

| Wavelength | 1.54178 Å | |
| --- | --- | --- |
| Crystal system | Monoclinic | |
| Space group | $P2_1$ | |
| Unit cell dimensions | a = 7.7692(12) Å | α = 90° |
| | b = 5.1020(9) Å | β = 105.458(9)° |
| | c = 10.3795(16) Å | γ = 90° |
| Volume | 396.54(11) Å$^3$ | |
| Z | 2 | |
| Density (calculated) | 1.470 Mg/m$^3$ | |
| Reflections collected | 2875 | |
| Independent reflections | 1097 [R(int) = 0.0260] | |
| Final R indices [I > 2sigma(I)] | R1 = 0.0311, wR2 = 0.0851 | |
| R indices (all data) | R1 = 0.0330, wR2 = 0.0866 | |

Example 15

LICPRO2

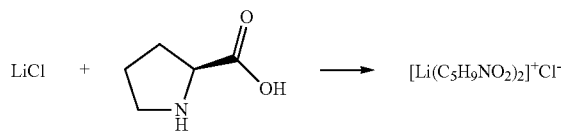

Lithium chloride (99%, anhydrous, used as received from Acros Organics, 0.50 g, 11.8 mmol) and L-proline (99+% pure, used as received from Acros Organics, 2.72 g, 23.6 mmol) were dissolved in 2.0 ml of hot deionised water. It was maintained on the hot plate until crystals emerged from the hot solution. Colourless block crystals (1266 mg) were harvested from the hot solution.

Melting point=250° C.

Crystals of LICPRO2 were characterized by FT-IR spectroscopy, DSC, TGA, powder x-ray diffraction, and single crystal x-ray crystallography (Table 15).

The single crystal x-ray structural analysis reveals that LICPRO2 contains four lithium cations, four chloride anions and eight L-proline molecules in the unit cell. Each lithium cation is bridged by four carboxylates to form a cationic diamondoid net with hexagonal channels exhibiting diameters ranging from 10.1 Å to 12.5 Å, populated by the chloride anions. The framework is reinforced by hydrogen bonding between the carboxylate of one amino acid and the ammonium of an adjacent amino acid [N—H•••O, 2.7404 (15) Å]. The presence of pairs of chloride anions [N—H•••Cl, 3.1322(12) Å] in these hexagonal channels interacting with neighboring ammonium groups renders interpenetration impossible

TABLE 15

Single crystal x-ray diffraction data for LICPRO2
(Bruker-AXS APEX2 CCD diffractometer)
Crystallographic data

| Empirical formula | [Li(C$_5$H$_9$NO$_2$)$_2$]$^+$Cl$^-$ | |
| --- | --- | --- |
| Formula weight | 272.65 | |
| Temperature | 100(2) K | |
| Wavelength | 1.54178 Å | |
| Crystal system | Tetragonal | |
| Space group | $P4_12_12$ | |
| Unit cell dimensions | a = 9.0791(1) Å | α = 90° |
| | b = 9.079(1) Å | β = 90° |
| | c = 15.4104(2) Å | γ = 90° |
| Volume | 1270.28(3) Å$^3$ | |
| Z | 4 | |
| Density (calculated) | 1.426 Mg/m$^3$ | |
| Reflections collected | 10850 | |
| Independent reflections | 1150 [R(int) = 0.0417] | |
| Final R indices [I > 2sigma(I)] | R1 = 0.0229, wR2 = 0.0662 | |
| R indices (all data) | R1 = 0.0231, wR2 = 0.0663 | |

Example 16

LICDMG

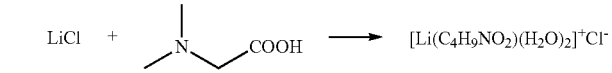

Lithium chloride (99%, anhydrous, used as received from Acros Organics, 50.0 mg, 1.18 mmol) and N,N-dimethylglycine (97% pure, used as received from Acros Organics, 122.0 mg, 1.18 mmol) were dissolved in 0.75 ml of hot deionised water. It was left for slow evaporation. Colorless block crystals (101 mg) were harvested after one month.

Melting point=272° C.

Crystals of LICDMG were characterized by FT-IR spectroscopy, DSC, TGA, powder x-ray diffraction, and single crystal x-ray crystallography (Table 16).

The single crystal x-ray structural analysis reveals that LICDMG contains two lithium cations, two chloride anions, two N,N-dimethylglycine molecules and four water molecules in the unit cell. Two carboxylates bridge two lithium cations to form an eight-membered ring. Two water molecules are coordinated to each lithium cation to fulfil the tetrahedral coordination environment of lithium cations. The chloride anions act as hydrogen bond acceptors towards three water molecules and an ammonium group.

TABLE 16

Single crystal x-ray diffraction data for LICDMG
(Bruker-AXS APEX2 CCD diffractometer)
Crystallographic data

| Empirical formula | [Li(C$_4$H$_9$NO$_2$)(H$_2$O)$_2$]$^+$Cl$^-$ | |
| --- | --- | --- |
| Formula weight | 181.55 | |
| Temperature | 100(2) K | |
| Wavelength | 1.54178 Å | |
| Crystal system | Triclinic | |
| Space group | P-1 | |
| Unit cell dimensions | a = 7.20900(10) Å | α = 110.7460(10)° |
| | b = 7.5745(2) Å | β = 93.1700(10)° |
| | c = 9.0100(2) Å | γ = 103.7090(10)° |
| Volume | 441.698(16) Å$^3$ | |
| Z | 2 | |
| Density (calculated) | 1.522 Mg/m$^3$ | |
| Reflections collected | 3766 | |
| Independent reflections | 1466 [R(int) = 0.0331] | |
| Final R indices [I > 2sigma(I)] | R1 = 0.0290, wR2 = 0.0760 | |
| R indices (all data) | R1 = 0.0298, wR2 = 0.0766 | |

Example 17

LICDMG2

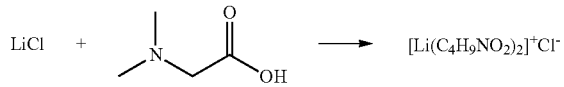

Lithium chloride (99%, anhydrous, used as received from Acros Organics, 0.5 g, 11.8 mmol) and N,N-dimethylglycine (used as received from Alfa Aesar, 2.44 g, 23.6 mmol) were dissolved in 3.0 ml of hot deionised water. It was maintained on the hot plate until crystals emerged from the hot solution. Colourless block crystals (1488 mg) were collected from the hot solution.

Crystals of LICDMG2 were characterized by FT-IR spectroscopy, powder x-ray diffraction, and single crystal x-ray crystallography (Table 17).

The single crystal x-ray structural analysis reveals that LICDMG2 contains eight lithium cations, eight chloride anions and sixteen N,N-dimethylglycine molecules in the unit cell. Each lithium cation is bridged by four carboxylates to form a cationic diamondoid net with hexagonal channels exhibiting diameters ranging from 10.6 Å to 12.0 Å, populated by the chloride anions. The framework is reinforced by hydrogen bonding between the carboxylate of one amino acid and the ammonium of an adjacent amino acid [N—H•••O, 2.742(2) Å]. The presence of pairs of chloride anions [C—H•••Cl, 3.628 Å, 3.633 Å and 3.635 Å] in these hexagonal channels interacting with neighboring methyl groups renders interpenetration impossible.

TABLE 17

Single crystal x-ray diffraction data for LICDMG2
(Bruker-AXS APEX2 CCD diffractometer)
Crystallographic data

| | |
|---|---|
| Empirical formula | $[Li(C_4H_9NO_2)_2]^+Cl^-$ |
| Formula weight | 248.63 |
| Temperature | 100(2) K |
| Wavelength | 1.54178 Å |
| Crystal system | Orthorhombic |
| Space group | Fdd2 |
| Unit cell dimensions | a = 14.0427(5) Å   α = 90° |
| | b = 14.6533(5) Å   β = 90° |
| | c = 12.4822(4) Å   γ = 90° |
| Volume | 2568.49(15) Å$^3$ |
| Z | 8 |
| Density (calculated) | 1.286 Mg/m$^3$ |
| Reflections collected | 5300 |
| Independent reflections | 1080 [R(int) = 0.0577] |
| Final R indices [I > 2sigma(I)] | R1 = 0.0312, wR2 = 0.0726 |
| R indices (all data) | R1 = 0.0342, wR2 = 0.0738 |

Example 18

LICBAL

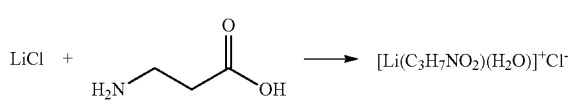

Lithium chloride (99%, anhydrous, used as received from Acros Organics, 1.00 g, 23.6 mmol) and β-alanine (99-F % pure, used as received from Acros Organics, 2.11 g, 23.6 mmol) were dissolved in 2.0 ml of hot deionised water. It was maintained on the hot plate until crystals emerged from the hot solution. The contents were allowed to cool. The mother liquor was decanted and 0.5 ml of deionised water was added. The colorless plate crystals (1910 mg) were harvested the next day.

Melting point=252° C.

Crystals of LICBAL were characterized by FT-IR spectroscopy, DSC, TGA, powder x-ray diffraction, and single crystal x-ray crystallography (Table 18).

The single crystal x-ray structural analysis reveals that LICBAL contains four lithium cations, four chloride anions, four β-alanine molecules and four water molecules in the unit cell. Three carboxylates bridge one lithium cation to form a chain of fused six-membered ring. The tetrahedral coordination environment of the lithium cations is achieved by three bridging carboxylates and a water molecule. Each chloride anion acts as hydrogen bond acceptors towards two water molecules and two ammonium ($RNH_3^+$) groups.

TABLE 18

Single crystal x-ray diffraction data for LICBAL
(Bruker-AXS APEX2 CCD diffractometer)
Crystallographic data

| | |
|---|---|
| Empirical formula | $[Li(C_3H_7NO_2)(H_2O)]^+Cl^-$ |
| Formula weight | 149.50 |
| Temperature | 100(2) K |
| Wavelength | 1.54178 Å |
| Crystal system | Monoclinic |
| Space group | P2$_1$/n |
| Unit cell dimensions | a = 6.6716(9) Å   α = 90° |
| | b = 5.0400(8) Å   β = 95.888(7)° |
| | c = 19.816(3) Å   γ = 90° |
| Volume | 662.78(16) Å$^3$ |
| Z | 4 |
| Density (calculated) | 1.498 Mg/m$^3$ |
| Reflections collected | 5332 |
| Independent reflections | 1156 [R(int) = 0.0427] |
| Final R indices [I > 2sigma(I)] | R1 = 0.0288, wR2 = 0.0748 |
| R indices (all data) | R1 = 0.0302, wR2 = 0.0757 |

Example 19

LICBAL-Anhydrate

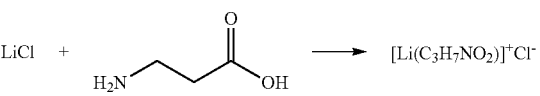

Lithium chloride (99%, anhydrous, used as received from Acros Organics, 1.00 g, 23.6 mmol) and β-alanine (99-F % pure, used as received from Acros Organics, 2.11 g, 23.6 mmol) were dissolved in 2.0 ml of hot deionised water. It was maintained on the hot plate until crystals emerged from the hot solution. Colourless rod crystals (2143 mg) were collected from the hot solution.

Melting point=252° C.

Crystals of LICBAL-anhydrate were characterized by FT-IR spectroscopy, DSC, TGA, powder x-ray diffraction, and single crystal x-ray crystallography (Table 19).

The single crystal x-ray structural analysis reveals that LICBAL-anhydrite contains four lithium cations, four chloride anions and four β-alanine molecules in the unit cell. Two carboxylates bridge two lithium cations to form an eight-membered ring. Adjacent eight-membered rings are connected by a bridging carboxylate and lithium cation to form a 4-membered ring. The tetrahedral coordination environment of the lithium cations is achieved by three bridging carboxylates and a chloride anion. Each ammonium group ($RNH_3^+$) forms two hydrogen bonds to two different chloride anions and a hydrogen bond to an adjacent carboxylate.

TABLE 19

Single crystal x-ray diffraction data for LICBAL-anhydrate
(Bruker-AXS APEX2 CCD diffractometer)
Crystallographic data

| | |
|---|---|
| Empirical formula | $[Li(C_3H_7NO_2)]^+Cl^-$ |
| Formula weight | 131.49 |
| Temperature | 100(2) K |
| Wavelength | 1.54178 Å |
| Crystal system | Monoclinic |
| Space group | $P2_1/n$ |
| Unit cell dimensions | a = 5.0510(2) Å   α = 90° |
| | b = 13.2649(5) Å   β = 96.721(2)° |
| | c = 8.9413(3) Å   γ = 90° |
| Volume | 594.96(4) Å³ |
| Z | 4 |
| Density (calculated) | 1.252 Mg/m³ |
| Reflections collected | 4986 |
| Independent reflections | 1045 [R(int) = 0.0411] |
| Final R indices [I > 2sigma(I)] | R1 = 0.0281, wR2 = 0.0730 |
| R indices (all data) | R1 = 0.0296, wR2 = 0.0737 |

Example 20

LICABA

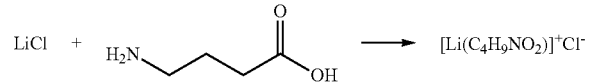

Lithium chloride (99%, anhydrous, used as received from Acros Organics, 1.00 g, 23.6 mmol) and 4-aminobutyric acid (99% pure, used as received from Acros Organics, 2.44 g, 23.6 mmol) were dissolved in 2.0 ml of hot deionised water. It was maintained on the hot plate until crystals emerged from the hot solution. Colorless rod crystals (2244 mg) were collected from the hot solution.

Melting point=241° C.

Crystals of LICABA were characterized by FT-IR spectroscopy, DSC, TGA, powder x-ray diffraction, and single crystal x-ray crystallography (Table 20).

The single crystal x-ray structural analysis reveals that LICABA contains four lithium cations, four chloride anions and four 4-aminobutyric acid molecules in the unit cell. Three carboxylates bridge one lithium cations to form a linear chain of six-membered ring. The tetrahedral coordination environment of the lithium cations were achieved by three bridging carboxylates and a chloride anion. Each ammonium group ($RNH_3^+$) forms two hydrogen bonds to two chloride anions and a hydrogen bond to an adjacent carboxylate.

TABLE 20

Single crystal x-ray diffraction data for LICABA
(Bruker-AXS APEX2 CCD diffractometer)
Crystallographic data

| | |
|---|---|
| Empirical formula | $[Li(C_4H_9NO_2)]^+Cl^-$ |
| Formula weight | 145.51 |
| Temperature | 100(2) K |
| Wavelength | 1.54178 Å |
| Crystal system | Monoclinic |
| Space group | C2/c |
| Unit cell dimensions | a = 20.0021(4) Å   α = 90° |
| | b = 4.88150(10) Å   β = 124.9290(10)° |
| | c = 17.0417(6) Å   γ = 90° |
| Volume | 1364.21(6) Å³ |
| Z | 4 |
| Density (calculated) | 1.417 Mg/m³ |
| Reflections collected | 5451 |
| Independent reflections | 1214 [R(int) = 0.0400] |
| Final R indices [I > 2sigma(I)] | R1 = 0.0298, wR2 = 0.0776 |
| R indices (all data) | R1 = 0.0312, wR2 = 0.0783 |

Example 21

LINPRO2—Forms I & II

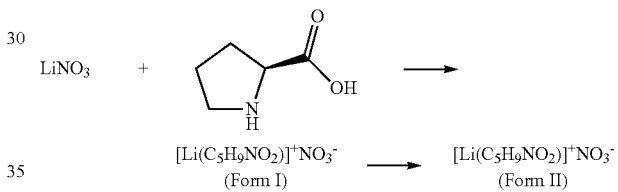

Lithium nitrate (98%, anhydrous, used as received from Fluka, 413.4 mg, 6.0 mmol) and L-proline (99+% pure, used as received from Acros Organics, 1381.2 mg, 12.0 mmol) were dissolved in 2.0 ml of hot deionised water. It was maintained on the hot plate until crystals emerged from the hot solution. Colorless plates (Form I, metastable form) were collected from the hot solution which in due course of time transform to 3-D rhombohedral crystals (Form II, 603 mg) once they are removed from the hot plate.

Melting point=176.1° C. (Form II).

Crystals of LINPRO2 Forms I and II were characterized by single crystal X-ray crystallography (Tables 21a and 21b). LINPRO2, Form II, crystals were also analyzed by FT-IR spectroscopy, DSC, TGA, and powder X-ray diffraction.

The single crystal x-ray structural analysis reveals that LINPRO2, Form I (metastable form), contains two lithium cations, two nitrate anions and four L-proline molecules in the asymmetric unit. Each lithium is coordinated by four bridging carboxylate and the overall structure results in the formation of zeolite ABW framework. LINPRO2, Form II, contains one lithium cation, one nitrate anion and two L-proline molecules in the asymmetric unit. Each lithium is coordinated by four bridging carboxylate and the overall structure results in the formation of diamondoid network. In both the forms the ammonium cations ($R_2NH_2^+$) hydrogen bond to the nitrate anions and a hydrogen bond to an adjacent carboxylate.

TABLE 21a

Single crystal X-ray diffraction data for LINPRO2-Form I
(Bruker-AXS APEX2 CCD diffractometer)
Crystallographic data

| | |
|---|---|
| Empirical formula | $C_{10}H_{18}N_3O_7Li$ |
| Formula weight | 299.21 |
| Temperature | 100 (2) K |
| Wavelength | 1.54178 Å |
| Crystal system | Orthorhombic |
| Space group | $P2_12_12_1$ |
| Unit cell dimensions | a = 11.0448(3) Å  α = 90° |
| | b = 12.0393(3) Å  β = 90° |
| | c = 20.2019(5) Å  γ = 90° |
| Volume | 2687.34 Å$^3$ |
| Z | 8 |
| Density (calculated) | 1.480 Mg/m$^3$ |
| Reflections collected | 15510 |
| Independent reflections | 4505 [R(int) = 0.0458] |
| Final R indices [I > 2sigma(I)] | R1 = 0.0314, wR2 = 0.0799 |
| R indices (all data) | R1 = 0.0337, wR2 = 0.0812 |

TABLE 21b

Single crystal X-ray diffraction data for LINPRO2-Form II
(Bruker-AXS APEX2 CCD diffractometer)
Crystallographic data

| | |
|---|---|
| Empirical formula | $C_{10}H_{18}N_3O_7Li$ |
| Formula weight | 299.21 |
| Temperature | 100 (2) K |
| Wavelength | 1.54178 Å |
| Crystal system | Orthorhombic |
| Space group | $P2_12_12_1$ |
| Unit cell dimensions | a = 9.4746 (5) Å  α = 90° |
| | b = 9.5817 (5) Å  β = 90° |
| | c = 15.0372 (7) Å  γ = 90° |
| Volume | 1362.97 Å$^3$ |
| Z | 4 |
| Density (calculated) | 1.456 Mg/m$^3$ |
| Reflections collected | 9047 |
| Independent reflections | 2308 [R(int) = 0.0545] |
| Final R indices [I > 2sigma(I)] | R1 = 0.1164, wR2 = 0.3273 |
| R indices (all data) | R1 = 0.1177, wR2 = 0.3279 |

Example 22

LiCl-Leucine

LiCl-Leucine cocrystals were synthesized according to the following steps: Lithium chloride, anhydrous, 253.8 mg (6.0 mmol) and L-leucine, 40 mg (0.3 mmol) were dissolved in 5 mL of deionized water and evaporated on a hot plate until needle-like crystals emerged from the hot solution. The crystals were transferred into another vial and capped.

Figure 4:
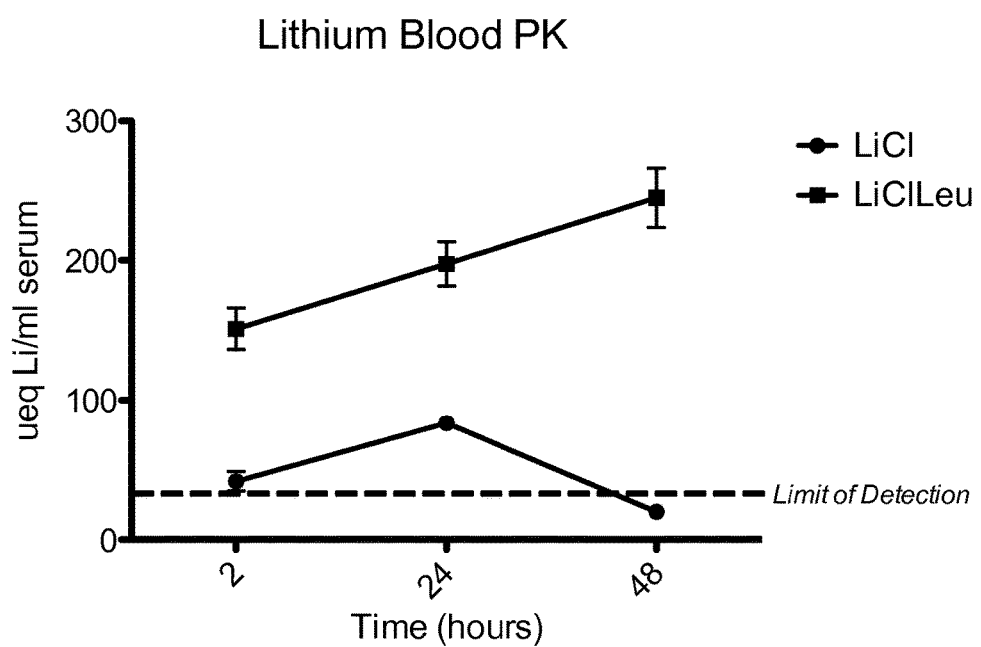
FIG. 4 is a graph depicting the effective absorption rate of LiCl-Leu in comparison to LiCl at 2, 24, and 48 hours as described in greater detail in Example 22.
Figure 5:
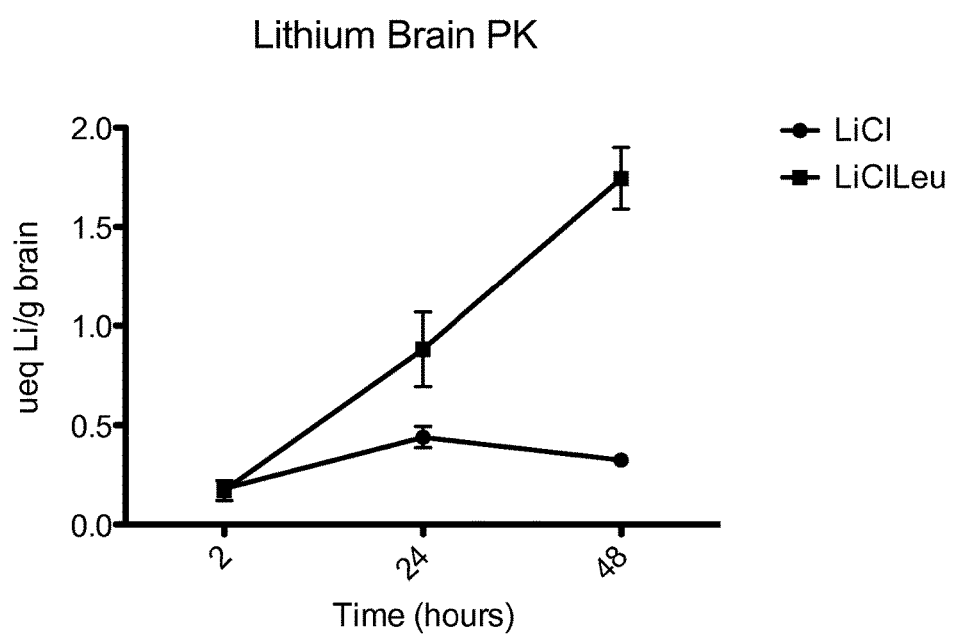
FIG. 5 is a graph depicting the concentration of LiCl-Leu in the brain in comparison to LiCl at 2, 24, and 48 hours as described in greater detail in Example 22.

Using a power analysis, we determined that n=4 would be sufficient to achieve statistical significance. We dosed rats (n=4 per formulation group per time point) via oral gavage with 4 meq of lithium as LiCl and as LiCl-Leucine in an aqueous vehicle. The rats were euthanized at 2, 24, and 48 hours (FIG. 4). Approximately 3 ml of blood was collected in edta tubes via cardiac puncture. The animals were perfused with ice cold saline using a pressure-controlled perfusion pump. Perfused brains were collected and stored at −80° C. The lithium content in plasma and brain samples were quantified using atomic absorption spectroscopy (AAS). The data (see FIGS. 4 & 5) revealed that the LiCl-Leu was absorbed more effectively from the GI in comparison to LiCl. The data revealed that the LiCl-Leu was absorbed more effectively from the GI in comparison to LiCl. This is evidenced by high serum concentrations of lithium. These results were statistically significant at all time points (P<0.0001). Furthermore, the brain pharmacokinetic data supported our hypothesis that amino acids known to be actively transported into the brain could be used as cocrystal formers to improve BBB penetration of the active pharmaceutical ingredient (API). We measured higher concentrations of lithium in the brain when equivalent doses of the cocrystal were administered. Our data is statistically significant at 48 hours (P<0.0001). As a result, compositions of the present invention could be used to lower the oral dose required to achieve therapeutic concentrations of lithium in the brain, thus reducing the peripheral toxicity and potentially broadening the therapeutic index in comparison to conventional lithium forms.

REFERENCES (1) Wong, R.; Allen, F. H.; Willett, P. *Journal of Applied Crystallography* 2010, 43, 811.
(2) Baerlocher, C.; McCusker, L. B.; Olson, D. H. *Atlas of Zeolite Framework Types*; Sixth Revised ed.; Elsevier Science: Amsterdam, 2007.
(3) Cundy, C. S.; Cox, P. A. *Chemical Reviews* 2003, 103, 663.
(4) Zaworotko, M. J. *Chemical Society Reviews* 1994, 23, 283.
(5) Ockwig, N. W.; Delgado-Friedrichs, O.; O'Keeffe, M.; Yaghi, O. M. *Accounts of Chemical Research* 2005, 38, 176.
(6) Davis, M. E. *Nature* 2002, 417, 813.
(7) Lopez, S.; Kahraman, M.; Harmata, M.; Keller, S. W. *Inorganic Chemistry* 1997, 36, 6138.
(8) Evans, O. R.; Lin, W. B. *Accounts of Chemical Research* 2002, 35, 511.
(9) Keller, S. W. *Angewandte Chemie International Edition in English* 1997, 36, 247.
(10) Liang, K.; Zheng, H. G.; Song, Y. L.; Lappert, M. E.; Li, Y. Z.; Xin, X. Q.; Huang, Z. X.; Chen, J. T.; Lu, S. F. *Angewandte Chemie-International Edition* 2004, 43, 5776.
(11) Fang, Q.; Zhu, G.; Xue, M.; Sun, J.; Wei, Y.; Qiu, S.; Xu, R. *Angewandte Chemie International Edition* 2005, 44, 3845.
(12) Copp, S. B.; Holman, K. T.; Sangster, J. O. S.; Subramanian, S.; Zaworotko, M. J. *Journal of the Chemical Society, Dalton Transactions* 1995, 2233.
(13) Copp, S. B.; Subramanian, S.; Zaworotko, M. J. *Journal of the American Chemical Society* 1992, 114, 8719.
(14) Copp, S. B.; Subramanian, S.; Zaworotko, M. J. *Journal of the Chemical Society, Chemical Communications* 1993, 1078.
(15) Hayashi, H.; Cote, A. P.; Furukawa, H.; O/'Keeffe, M.; Yaghi, O. M. *Nat Mater* 2007, 6, 501.
(16) Park, K. S.; Ni, Z.; Côté, P.; Choi, J. Y.; Huang, R.; Uribe-Romo, F. J.; Chae, H. K.; O'Keeffe, M.; Yaghi, O. M. *Proceedings of the National Academy of Sciences* 2006, 103, 10186.
(17) Huang, X. C.; Lin, Y. Y.; Zhang, J. P.; Chen, X. M. *Angewandte Chemie International Edition* 2006, 45, 1557.
(18) Zhang, J.; Wu, T.; Zhou, C.; Chen, S.; Feng, P.; Bu, X. *Angewandte Chemie* 2009, 121, 2580.
(19) Liu, Y.; Kravtsov, V. C.; Larsen, R.; Eddaoudi, M. *Chemical Communications* 2006, 1488.
(20) Alkordi, M. H.; Brant, J. A.; Wojtas, L.; Kravtsov, V. C.; Cairns, A. J.; Eddaoudi, M. *Journal of the American Chemical Society* 2009, 131, 17753.

(21) Navarro, J. A. R.; Barea, E.; Salas, J. M.; Masciocchi, N.; Galli, S.; Sironi, A.; Ania, C. O.; Parra, J. B. *Inorganic Chemistry* 2006, 45, 2397.
(22) Sava, D. F.; Kravtsov, V. C.; Nouar, F.; Wojtas, L.; Eubank, J. F.; Eddaoudi, M. *Journal of the American Chemical Society* 2008, 130, 3768.
(23) Hasche, S.; Mock, C.; Otto, J.; Schweppe, F.; Kirschbaum, K.; Krebs, B.; Pinkerton, A. A. *Inorganica Chimica Acta* 2000, 298, 9.
(24) Wu, T.; Zhang, J.; Zhou, C.; Wang, L.; Bu, X.; Feng, P. *Journal of the American Chemical Society* 2009, 131, 6111.
(25) Abrahams, B.; Grannas, M.; Hudson, T.; Robson, R. *Angewandte Chemie International Edition* 2010, 49, 1087.
(26) Morris, J. J.; Noll, B. C.; Henderson, K. W. *Crystal Growth & Design* 2006, 6, 1071.
(27) Banerjee, D.; Kim, S. J.; Li, W.; Wu, H.; Li, J.; Borkowski, L. A.; Philips, B. L.; Parise, J. B. *Crystal Growth & Design* 2010, 10, 2801.
(28) Saravanan, K.; Nagarathinam, M.; Balaya, P.; Vittal, J. J. *Journal of Materials Chemistry* 2010, 20, 8329.
(29) Wang, Z. M.; Zhang, B.; Fujiwara, H.; Kobayashi, H.; Kurmoo, M. *Chemical Communications* 2004, 416.
(30) Sreenivasulu, B.; Vittal, J. J. *Crystal Growth & Design* 2003, 3, 635.
(31) Chen, Z. L.; Jiang, C. F.; Yan, W. H.; Liang, F. P.; Batten, S. R. *Inorganic Chemistry* 2009, 48, 4674.
(32) Baran, J.; Drozd, M.; Ratajczak, H.; Pietraszko, A. *Journal of Molecular Structure* 2009, 927, 43.
(33) Barrer, R. M.; White, E. A. D. *Journal of the Chemical Society* (*Resumed*) 1951, 1267.
(34) Aiello, R.; Barrer R, M.; Kerr I, S. In *Molecular Sieve Zeolites-I*; AMERICAN CHEMICAL SOCIETY: 1974; Vol. 101, p 44.

What is claimed is:

1. A pharmaceutical composition comprising a lithium cocrystal solid composition and one or more of pharmaceutically acceptable pharmaceutically acceptable carriers, diluents, adjuvants, excipients, or vehicles,
   wherein the lithium cocrystal composition comprises a lithium salt and a neutral organic molecule in a stoichiometric ratio;
   wherein the lithium solid cocrystal composition has the formula LiX.aM or LiX.aM.bS wherein X is a halide or a pharmaceutically acceptable oxyanion, M is a neutral organic molecule, a is 1 or 2, b is 0, 0.5, 1.0, 1.5, 2.0, 2.5 or 3.0, and S is solvent or water; and wherein M is leucine and X is chloride.

2. A pharmaceutical composition comprising an active agent and one or more of pharmaceutically acceptable carriers, diluents, adjuvants, excipients, or vehicles,
   wherein the active agent is a solid lithium cocrystal composition comprising a lithium salt and a neutral organic molecule in a stoichiometric ratio;
   wherein the lithium solid cocrystal composition has the formula LiX.aM or LiX.aM.bS wherein X is a chloride, M is leucine, a is 1 or 2, b is 0, 0.5, 1.0, 1.5, 2.0, 2.5 or 3.0, and S is solvent or water; and
   wherein the pharmaceutical composition is in a dosage unit form comprising a predetermined amount of the active agent.

3. The pharmaceutical composition of claim 2, wherein the active agent is in a therapeutic amount effective to treat mood disorders or suicidality in a subject in need thereof.

4. The pharmaceutical composition of claim 2 wherein the dosage unit form is a tablet or capsule for oral administration.

* * * * *